United States Patent [19]
Anderson et al.

[11] Patent Number: 6,017,729
[45] Date of Patent: *Jan. 25, 2000

[54] RECEPTOR ACTIVATOR OF NF-κB

[75] Inventors: Dirk M. Anderson; Laurent Galibert, both of Seattle, Wash.; Eugene Maraskovsky, Caulfield Nth, Australia

[73] Assignee: Immunex Corporation, Seattle, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/996,139

[22] Filed: Dec. 22, 1997

Related U.S. Application Data

[60] Provisional application No. 60/064,671, Oct. 14, 1997, provisional application No. 60/077,181, Mar. 7, 1997, and provisional application No. 60/059,978, Dec. 23, 1996.

[51] Int. Cl.[7] .......................... C07H 21/04; C12N 15/12; C12N 15/63

[52] U.S. Cl. .................. 435/69.1; 435/70.1; 435/320.1; 435/325; 435/235.1; 435/23.1; 435/24.31; 435/252.3; 435/172.3; 536/23.1; 536/24.31; 530/350

[58] Field of Search ................................. 435/69.1, 70.1, 435/320.1, 325, 235.1, 252.3, 172.3; 536/23.1, 24.31; 530/350

[56] References Cited

FOREIGN PATENT DOCUMENTS

| | | |
|---|---|---|
| 0816380 A1 | 1/1998 | European Pat. Off. . |
| 0 873 998 A2 | 4/1998 | European Pat. Off. . |
| 0 911 342 A1 | 4/1998 | European Pat. Off. . |
| WO 93/08207 | 4/1993 | WIPO . |
| WO 96/34095 | 10/1996 | WIPO . |
| WO 97/23614 | 7/1997 | WIPO . |
| WO 98/25958 | 12/1997 | WIPO . |
| WO 98/28423 | 12/1997 | WIPO . |
| WO 98/46751 | 4/1998 | WIPO . |
| WO 98/54201 | 5/1998 | WIPO . |

OTHER PUBLICATIONS

Yasuda et al., *Proc. Natl. Acad. Sci.* 95:3597; 1998.

Suda et al., *Endocr. Rev.* 13:66; 1992.

Suda et al., *Bone* 17:87S; 1995.

Suda et al., in *Endocrine Review Monographs.* eds. Bikle, D.D. & Negrovilar, A. (Endocrine Soc., Bethesda), vol. 4, pp. 266–270; 1995.

Lacey et al., *Cell* 93:165; 1998.

Anderson et al., *Nature* 390:175; 1997.

EMBL Database entry HS421358; Accession No. W74421, Jun. 21, 1996; Hillier et al.: Homo sapiens cDNA clone 346544 contains Alu repetitive element.

GenEmbl Database Accesion No. X15271, Locus.HSTRGV3F, Human T–cell receptor gamma. Lefranc, M.P.

George et al., Current Methods in Sequence Comparison and Analysis, selected methods and applications. Edited by David H. Schlesinger, alan R. Liss, Inc., New York, pp 124–129 1988.

Embl–est Database Accession No.R03478, yq16f06.rl Homo Sapian cDNA clone 197123 5' sequence. Submitted by Hillier et al. Aug. 29, 1995.

*Primary Examiner*—Elizabeth Kemmerer
*Assistant Examiner*—Nirmal S. Basi
*Attorney, Agent, or Firm*—Janis C. Henry

[57] ABSTRACT

Isolated receptors, DNAs encoding such receptors, and pharmaceutical compositions made therefrom, are disclosed. The isolated receptors can be used to regulate an immune response. The receptors are also useful in screening for inhibitors thereof.

14 Claims, 3 Drawing Sheets

SEQUENCE LISTING

```
(1) GENERAL INFORMATION:

(iii) NUMBER OF SEQUENCES: 19

(2) INFORMATION FOR SEQ ID NO:1:

(i) SEQUENCE CHARACTERISTICS:
          (A) LENGTH: 3115 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: HOMO SAPIENS (vii) IMMEDIATE SOURCE:
          (A) LIBRARY: BONE-MARROW DERIVED DENDRITIC CELLS
          (B) CLONE: 9D-8A (ix) FEATURE:
          (A) NAME/KEY: CDS
          (B) LOCATION: 93..1868

(xi) SEQUENCE DESCRIPTION: SEQ ID NO:1:

GCTGCTGCTG CTCTGCGCGC TGCTCGCCCG GCTGCAGTTT TATCCAGAAA GAGCTGTGTG      60
```

| | |
|---|---|
| GACTCTCTGC CTGACCTCAG TGTTCTTTTC AG GTG GCT TTG CAG ATC GCT CCT<br>                                                                Val Ala Leu Gln Ile Ala Pro<br>                                                                1             5 | 113 |
| CCA TGT ACC AGT GAG AAG CAT TAT GAG CAT CTG GGA CGG TGC TGT AAC<br>Pro Cys Thr Ser Glu Lys His Tyr Glu His Leu Gly Arg Cys Cys Asn<br>         10                 15                       20 | 161 |
| AAA TGT GAA CCA GGA AAG TAC ATG TCT TCT AAA TGC ACT ACT ACC TCT<br>Lys Cys Glu Pro Gly Lys Tyr Met Ser Ser Lys Cys Thr Thr Thr Ser<br> 25                     30                       35 | 209 |
| GAC AGT GTA TGT CTG CCC TGT GGC CCG GAT GAA TAC TTG GAT AGC TGG<br>Asp Ser Val Cys Leu Pro Cys Gly Pro Asp Glu Tyr Leu Asp Ser Trp<br> 40                     45                       50                       55 | 257 |
| AAT GAA GAA GAT AAA TGC TTG CTG CAT AAA GTT TGT GAT ACA GGC AAG<br>Asn Glu Glu Asp Lys Cys Leu Leu His Lys Val Cys Asp Thr Gly Lys<br>                60                       65                       70 | 305 |
| GCC CTG GTG GCC GTG GTC GCC GGC AAC AGC ACG ACC CCC CGG CGC TGC<br>Ala Leu Val Ala Val Val Ala Gly Asn Ser Thr Thr Pro Arg Arg Cys<br>              75                       80                       85 | 353 |
| GCG TGC ACG GCT GGG TAC CAC TGG AGC CAG GAC TGC GAG TGC TGC CGC<br>Ala Cys Thr Ala Gly Tyr His Trp Ser Gln Asp Cys Glu Cys Cys Arg<br>         90                 95                       100 | 401 |
| CGC AAC ACC GAG TGC GCG CCG GGC CTG GGC GCC CAG CAC CCG TTG CAG<br>Arg Asn Thr Glu Cys Ala Pro Gly Leu Gly Ala Gln His Pro Leu Gln<br>105                     110                       115 | 449 |
| CTC AAC AAG GAC ACA GTG TGC AAA CCT TGC CTT GCA GGC TAC TTC TCT<br>Leu Asn Lys Asp Thr Val Cys Lys Pro Cys Leu Ala Gly Tyr Phe Ser<br>120                     125                       130                       135 | 497 |
| GAT GCC TTT TCC TCC ACG GAC AAA TGC AGA CCC TGG ACC AAC TGT ACC<br>Asp Ala Phe Ser Ser Thr Asp Lys Cys Arg Pro Trp Thr Asn Cys Thr<br>                140                       145                       150 | 545 |
| TTC CTT GGA AAG AGA GTA GAA CAT CAT GGG ACA GAG AAA TCC GAT GCG<br>Phe Leu Gly Lys Arg Val Glu His His Gly Thr Glu Lys Ser Asp Ala<br>              155                       160                       165 | 593 |
| GTT TGC AGT TCT TCT CTG CCA GCT AGA AAA CCA CCA AAT GAA CCC CAT<br>Val Cys Ser Ser Ser Leu Pro Ala Arg Lys Pro Pro Asn Glu Pro His<br>              170                       175                       180 | 641 |
| GTT TAC TTG CCC GGT TTA ATA ATT CTG CTT CTC TTC GCG TCT GTG GCC<br>Val Tyr Leu Pro Gly Leu Ile Ile Leu Leu Leu Phe Ala Ser Val Ala<br>              185                       190                       195 | 689 |
| CTG GTG GCT GCC ATC ATC TTT GGC GTT TGC TAT AGG AAA AAA GGG AAA<br>Leu Val Ala Ala Ile Ile Phe Gly Val Cys Tyr Arg Lys Lys Gly Lys<br>200                     205                       210                       215 | 737 |
| GCA CTC ACA GCT AAT TTG TGG CAC TGG ATC AAT GAG GCT TGT GGC CGC<br>Ala Leu Thr Ala Asn Leu Trp His Trp Ile Asn Glu Ala Cys Gly Arg<br>              220                       225                       230 | 785 |
| CTA AGT GGA GAT AAG GAG TCC TCA GGT GAC AGT TGT GTC AGT ACA CAC<br>Leu Ser Gly Asp Lys Glu Ser Ser Gly Asp Ser Cys Val Ser Thr His<br>                235                       240                       245 | 833 |
| ACG GCA AAC TTT GGT CAG CAG GGA GCA TGT GAA GGT GTC TTA CTG CTG<br>Thr Ala Asn Phe Gly Gln Gln Gly Ala Cys Glu Gly Val Leu Leu Leu<br>              250                       255                       260 | 881 |
| ACT CTG GAG GAG AAG ACA TTT CCA GAA GAT ATG TGC TAC CCA GAT CAA<br>Thr Leu Glu Glu Lys Thr Phe Pro Glu Asp Met Cys Tyr Pro Asp Gln<br>265                     270                       275 | 929 |
| GGT GGT GTC TGT CAG GGC ACG TGT GTA GGA GGT GGT CCC TAC GCA CAA<br>Gly Gly Val Cys Gln Gly Thr Cys Val Gly Gly Gly Pro Tyr Ala Gln<br>280                     285                       290                       295 | 977 |
| GGC GAA GAT GCC AGG ATG CTC TCA TTG GTC AGC AAG ACC GAG ATA GAG<br>Gly Glu Asp Ala Arg Met Leu Ser Leu Val Ser Lys Thr Glu Ile Glu<br>              300                       305                       310 | 1025 |

-continued

| | |
|---|---|
| GAA GAC AGC TTC AGA CAG ATG CCC ACA GAA GAT GAA TAC ATG GAC AGG<br>Glu Asp Ser Phe Arg Gln Met Pro Thr Glu Asp Glu Tyr Met Asp Arg<br>315                          320                     325 | 1073 |
| CCC TCC CAG CCC ACA GAC CAG TTA CTG TTC CTC ACT GAG CCT GGA AGC<br>Pro Ser Gln Pro Thr Asp Gln Leu Leu Phe Leu Thr Glu Pro Gly Ser<br>330                        335                     340 | 1121 |
| AAA TCC ACA CCT CCT TTC TCT GAA CCC CTG GAG GTG GGG GAG AAT GAC<br>Lys Ser Thr Pro Pro Phe Ser Glu Pro Leu Glu Val Gly Glu Asn Asp<br>345                        350                     355 | 1169 |
| AGT TTA AGC CAG TGC TTC ACG GGG ACA CAG AGC ACA GTG GGT TCA GAA<br>Ser Leu Ser Gln Cys Phe Thr Gly Thr Gln Ser Thr Val Gly Ser Glu<br>360                        365                     370                     375 | 1217 |
| AGC TGC AAC TGC ACT GAG CCC CTG TGC AGG ACT GAT TGG ACT CCC ATG<br>Ser Cys Asn Cys Thr Glu Pro Leu Cys Arg Thr Asp Trp Thr Pro Met<br>                    380                     385                     390 | 1265 |
| TCC TCT GAA AAC TAC TTG CAA AAA GAG GTG GAC AGT GGC CAT TGC CCG<br>Ser Ser Glu Asn Tyr Leu Gln Lys Glu Val Asp Ser Gly His Cys Pro<br>                    395                     400                     405 | 1313 |
| CAC TGG GCA GCC AGC CCC AGC CCC AAC TGG GCA GAT GTC TGC ACA GGC<br>His Trp Ala Ala Ser Pro Ser Pro Asn Trp Ala Asp Val Cys Thr Gly<br>          410                     415                     420 | 1361 |
| TGC CGG AAC CCT CCT GGG GAG GAC TGT GAA CCC CTC GTG GGT TCC CCA<br>Cys Arg Asn Pro Pro Gly Glu Asp Cys Glu Pro Leu Val Gly Ser Pro<br>425                        430                     435 | 1409 |
| AAA CGT GGA CCC TTG CCC CAG TGC GCC TAT GGC ATG GGC CTT CCC CCT<br>Lys Arg Gly Pro Leu Pro Gln Cys Ala Tyr Gly Met Gly Leu Pro Pro<br>440                        445                     450                     455 | 1457 |
| GAA GAA GAA GCC AGC AGG ACG GAG GCC AGA GAC CAG CCC GAG GAT GGG<br>Glu Glu Glu Ala Ser Arg Thr Glu Ala Arg Asp Gln Pro Glu Asp Gly<br>                    460                     465                     470 | 1505 |
| GCT GAT GGG AGG CTC CCA AGC TCA GCG AGG GCA GGT GCC GGG TCT GGA<br>Ala Asp Gly Arg Leu Pro Ser Ser Ala Arg Ala Gly Ala Gly Ser Gly<br>                    475                     480                     485 | 1553 |
| AGC TCC CCT GGT GGC CAG TCC CCT GCA TCT GGA AAT GTG ACT GGA AAC<br>Ser Ser Pro Gly Gly Gln Ser Pro Ala Ser Gly Asn Val Thr Gly Asn<br>          490                     495                     500 | 1601 |
| AGT AAC TCC ACG TTC ATC TCC AGC GGG CAG GTG ATG AAC TTC AAG GGC<br>Ser Asn Ser Thr Phe Ile Ser Ser Gly Gln Val Met Asn Phe Lys Gly<br>505                        510                     515 | 1649 |
| GAC ATC ATC GTG GTC TAC GTC AGC CAG ACC TCG CAG GAG GGC GCG GCG<br>Asp Ile Ile Val Val Tyr Val Ser Gln Thr Ser Gln Glu Gly Ala Ala<br>520                        525                     530                     535 | 1697 |
| GCG GCT GCG GAG CCC ATG GGC CGC CCG GTG CAG GAG GAG ACC CTG GCG<br>Ala Ala Ala Glu Pro Met Gly Arg Pro Val Gln Glu Glu Thr Leu Ala<br>                    540                     545                     550 | 1745 |
| CGC CGA GAC TCC TTC GCG GGG AAC GGC CCG CGC TTC CCG GAC CCG TGC<br>Arg Arg Asp Ser Phe Ala Gly Asn Gly Pro Arg Phe Pro Asp Pro Cys<br>                    555                     560                     565 | 1793 |
| GGC GGC CCC GAG GGG CTG CGG GAG CCG GAG AAG GCC TCG AGG CCG GTG<br>Gly Gly Pro Glu Gly Leu Arg Glu Pro Glu Lys Ala Ser Arg Pro Val<br>          570                     575                     580 | 1841 |
| CAG GAG CAA GGC GGG GCC AAG GCT TGA GCGCCCCCA TGGCTGGGAG<br>Gln Glu Gln Gly Gly Ala Lys Ala<br>585                        590 | 1888 |
| CCCGAAGCTC GGAGCCAGGG CTCGCGAGGG CAGCACCGCA GCCTCTGCCC CAGCCCCGGC | 1948 |
| CACCCAGGGA TCGATCGGTA CAGTCGAGGA AGACCACCCG GCATTCTCTG CCCACTTTGC | 2008 |
| CTTCCAGGAA ATGGGCTTTT CAGGAAGTGA ATTGATGAGG ACTGTCCCCA TGCCCACGGA | 2068 |
| TGCTCAGCAG CCCGCCGCAC TGGGGCAGAT GTCTCCCCTG CCACTCCTCA AACTCGCAGC | 2128 |

```
AGTAATTTGT GGCACTATGA CAGCTATTTT TATGACTATC CTGTTCTGTG GGGGGGGGGT        2188

CTATGTTTTC CCCCCATATT TGTATTCCTT TTCATAACTT TTCTTGATAT CTTTCCTCCC        2248

TCTTTTTTAA TGTAAAGGTT TTCTCAAAAA TTCTCCTAAA GGTGAGGGTC TCTTTCTTTT        2308

CTCTTTTCCT TTTTTTTTTC TTTTTTTGGC AACCTGGCTC TGGCCCAGGC TAGAGTGCAG        2368

TGGTGCGATT ATAGCCCGGT GCAGCCTCTA ACTCCTGGGC TCAAGCAATC CAAGTGATCC        2428

TCCCACCTCA ACCTTCGGAG TAGCTGGGAT CACAGCTGCA GGCCACGCCC AGCTTCCTCC        2488

CCCCGACTCC CCCCCCCCAG AGACACGGTC CCACCATGTT ACCCAGCCTG GTCTCAAACT        2548

CCCCAGCTAA AGCAGTCCTC CAGCCTCGGC CTCCCAAAGT ACTGGGATTA CAGGCGTGAG        2608

CCCCCACGCT GGCCTGCTTT ACGTATTTTC TTTTGTGCCC CTGCTCACAG TGTTTTAGAG        2668

ATGGCTTTCC CAGTGTGTGT TCATTGTAAA CACTTTTGGG AAAGGGCTAA ACATGTGAGG        2728

CCTGGAGATA GTTGCTAAGT TGCTAGGAAC ATGTGGTGGG ACTTTCATAT CTGAAAAAT         2788

GTTCTATATT CTCATTTTTC TAAAAGAAAG AAAAAAGGAA ACCCGATTTA TTTCTCCTGA        2848

ATCTTTTTAA GTTTGTGTCG TTCCTTAAGC AGAACTAAGC TCAGTATGTG ACCTTACCCG        2908

CTAGGTGGTT AATTTATCCA TGCTGGCAGA GGCACTCAGG TACTTGGTAA GCAAATTTCT        2968

AAAACTCCAA GTTGCTGCAG CTTGGCATTC TTCTTATTCT AGAGGTCTCT CTGGAAAAGA        3028

TGGAGAAAAT GAACAGGACA TGGGGCTCCT GGAAAGAAAG GGCCCGGGAA GTTCAAGGAA        3088

GAATAAAGTT GAAATTTTAA AAAAAAA                                           3115

(2) INFORMATION FOR SEQ ID NO:2:

(i) SEQUENCE CHARACTERISTICS:
        (A) LENGTH: 591 amino acids
        (B) TYPE: amino acid
        (D) TOPOLOGY: linear (ii) MOLECULE TYPE: protein (xi) SEQUENCE DESCRIPTION: SEQ ID NO:2:

Val Ala Leu Gln Ile Ala Pro Pro Cys Thr Ser Glu Lys His Tyr Glu
  1               5                  10                  15

His Leu Gly Arg Cys Cys Asn Lys Cys Glu Pro Gly Lys Tyr Met Ser
             20                  25                  30

Ser Lys Cys Thr Thr Thr Ser Asp Ser Val Cys Leu Pro Cys Gly Pro
         35                  40                  45

Asp Glu Tyr Leu Asp Ser Trp Asn Glu Glu Asp Lys Cys Leu Leu His
     50                  55                  60

Lys Val Cys Asp Thr Gly Lys Ala Leu Val Ala Val Ala Gly Asn
 65                  70                  75                  80

Ser Thr Thr Pro Arg Arg Cys Ala Cys Thr Ala Gly Tyr His Trp Ser
             85                  90                  95

Gln Asp Cys Glu Cys Cys Arg Arg Asn Thr Glu Cys Ala Pro Gly Leu
            100                 105                 110

Gly Ala Gln His Pro Leu Gln Leu Asn Lys Asp Thr Val Cys Lys Pro
            115                 120                 125

Cys Leu Ala Gly Tyr Phe Ser Asp Ala Phe Ser Ser Thr Asp Lys Cys
        130                 135                 140

Arg Pro Trp Thr Asn Cys Thr Phe Leu Gly Lys Arg Val Glu His His
145                 150                 155                 160

Gly Thr Glu Lys Ser Asp Ala Val Cys Ser Ser Ser Leu Pro Ala Arg
                165                 170                 175

Lys Pro Pro Asn Glu Pro His Val Tyr Leu Pro Gly Leu Ile Ile Leu
```

```
                  180                 185                 190
Leu Leu Phe Ala Ser Val Ala Leu Val Ala Ala Ile Ile Phe Gly Val
            195                 200                 205
Cys Tyr Arg Lys Lys Gly Lys Ala Leu Thr Ala Asn Leu Trp His Trp
        210                 215                 220
Ile Asn Glu Ala Cys Gly Arg Leu Ser Gly Asp Lys Glu Ser Ser Gly
225                 230                 235                 240
Asp Ser Cys Val Ser Thr His Thr Ala Asn Phe Gly Gln Gln Gly Ala
                245                 250                 255
Cys Glu Gly Val Leu Leu Leu Thr Leu Glu Gly Lys Thr Phe Pro Glu
            260                 265                 270
Asp Met Cys Tyr Pro Asp Gln Gly Val Cys Gln Gly Thr Cys Val
        275                 280                 285
Gly Gly Gly Pro Tyr Ala Gln Gly Glu Asp Ala Arg Met Leu Ser Leu
    290                 295                 300
Val Ser Lys Thr Glu Ile Glu Glu Asp Ser Phe Arg Gln Met Pro Thr
305                 310                 315                 320
Glu Asp Glu Tyr Met Asp Arg Pro Ser Gln Pro Thr Asp Gln Leu Leu
                325                 330                 335
Phe Leu Thr Glu Pro Gly Ser Lys Ser Thr Pro Pro Phe Ser Glu Pro
            340                 345                 350
Leu Glu Val Gly Glu Asn Asp Ser Leu Ser Gln Cys Phe Thr Gly Thr
        355                 360                 365
Gln Ser Thr Val Gly Ser Glu Ser Cys Asn Cys Thr Glu Pro Leu Cys
    370                 375                 380
Arg Thr Asp Trp Thr Pro Met Ser Ser Glu Asn Tyr Leu Gln Lys Glu
385                 390                 395                 400
Val Asp Ser Gly His Cys Pro His Trp Ala Ala Ser Pro Ser Pro Asn
                405                 410                 415
Trp Ala Asp Val Cys Thr Gly Cys Arg Asn Pro Pro Gly Glu Asp Cys
            420                 425                 430
Glu Pro Leu Val Gly Ser Pro Lys Arg Gly Pro Leu Pro Gln Cys Ala
        435                 440                 445
Tyr Gly Met Gly Leu Pro Pro Glu Glu Glu Ala Ser Arg Thr Glu Ala
    450                 455                 460
Arg Asp Gln Pro Glu Asp Gly Ala Asp Gly Arg Leu Pro Ser Ser Ala
465                 470                 475                 480
Arg Ala Gly Ala Gly Ser Gly Ser Ser Pro Gly Gly Gln Ser Pro Ala
                485                 490                 495
Ser Gly Asn Val Thr Gly Asn Ser Asn Ser Thr Phe Ile Ser Ser Gly
            500                 505                 510
Gln Val Met Asn Phe Lys Gly Asp Ile Ile Val Val Tyr Val Ser Gln
        515                 520                 525
Thr Ser Gln Glu Gly Ala Ala Ala Ala Glu Pro Met Gly Arg Pro
    530                 535                 540
Val Gln Glu Glu Thr Leu Ala Arg Arg Asp Ser Phe Ala Gly Asn Gly
545                 550                 555                 560
Pro Arg Phe Pro Asp Pro Cys Gly Gly Pro Glu Gly Leu Arg Glu Pro
                565                 570                 575
Glu Lys Ala Ser Arg Pro Val Gln Glu Gln Gly Gly Ala Lys Ala
            580                 585                 590
```

(2) INFORMATION FOR SEQ ID NO:3:

-continued

```
    (i) SEQUENCE CHARACTERISTICS:
        (A) LENGTH: 1391 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (vii) IMMEDIATE SOURCE:
        (A) LIBRARY: BONE-MARROW DERIVED DENDRITIC CELLS
        (B) CLONE: 9D-15C (ix) FEATURE:
        (A) NAME/KEY: CDS
        (B) LOCATION: 39..1391

(xi) SEQUENCE DESCRIPTION: SEQ ID NO:3:
```

```
CCGCTGAGGC CGCGGCGCCC GCCAGCCTGT CCCGCGCC ATG GCC CCG CGC GCC            53
                                           Met Ala Pro Arg Ala
                                             1               5

CGG CGG CGC CGC CCG CTG TTC GCG CTG CTG CTG CTC TGC GCG CTG CTC         101
Arg Arg Arg Arg Pro Leu Phe Ala Leu Leu Leu Leu Cys Ala Leu Leu
                 10                  15                  20

GCC CGG CTG CAG GTG GCT TTG CAG ATC GCT CCT CCA TGT ACC AGT GAG         149
Ala Arg Leu Gln Val Ala Leu Gln Ile Ala Pro Pro Cys Thr Ser Glu
             25                  30                  35

AAG CAT TAT GAG CAT CTG GGA CGG TGC TGT AAC AAA TGT GAA CCA GGA         197
Lys His Tyr Glu His Leu Gly Arg Cys Cys Asn Lys Cys Glu Pro Gly
         40                  45                  50

AAG TAC ATG TCT TCT AAA TGC ACT ACT ACC TCT GAC AGT GTA TGT CTG         245
Lys Tyr Met Ser Ser Lys Cys Thr Thr Thr Ser Asp Ser Val Cys Leu
     55                  60                  65

CCC TGT GGC CCG GAT GAA TAC TTG GAT AGC TGG AAT GAA GAA GAT AAA         293
Pro Cys Gly Pro Asp Glu Tyr Leu Asp Ser Trp Asn Glu Glu Asp Lys
 70                  75                  80                  85

TGC TTG CTG CAT AAA GTT TGT GAT ACA GGC AAG GCC CTG GTG GCC GTG         341
Cys Leu Leu His Lys Val Cys Asp Thr Gly Lys Ala Leu Val Ala Val
                 90                  95                 100

GTC GCC GGC AAC AGC ACG ACC CCC CGG CGC TGC GCG TGC ACG GCT GGG         389
Val Ala Gly Asn Ser Thr Thr Pro Arg Arg Cys Ala Cys Thr Ala Gly
             105                 110                 115

TAC CAC TGG AGC CAG GAC TGC GAG TGC TGC CGC CGC AAC ACC GAG TGC         437
Tyr His Trp Ser Gln Asp Cys Glu Cys Cys Arg Arg Asn Thr Glu Cys
         120                 125                 130

GCG CCG GGC CTG GGC GCC CAG CAC CCG TTG CAG CTC AAC AAG GAC ACA         485
Ala Pro Gly Leu Gly Ala Gln His Pro Leu Gln Leu Asn Lys Asp Thr
135                 140                 145

GTG TGC AAA CCT TGC CTT GCA GGC TAC TTC TCT GAT GCC TTT TCC TCC         533
Val Cys Lys Pro Cys Leu Ala Gly Tyr Phe Ser Asp Ala Phe Ser Ser
150                 155                 160                 165

ACG GAC AAA TGC AGA CCC TGG ACC AAC TGT ACC TTC TTG GGA AAG AGA         581
Thr Asp Lys Cys Arg Pro Trp Thr Asn Cys Thr Phe Leu Gly Lys Arg
                 170                 175                 180

GTA GAA CAT CAT GGG ACA GAG AAA TCC GAT GCG GTT TGC AGT TCT TCT         629
Val Glu His His Gly Thr Glu Lys Ser Asp Ala Val Cys Ser Ser Ser
             185                 190                 195

CTG CCA GCT AGA AAA CCA CCA AAT GAA CCC CAT GTT TAC TTG CCC GGT         677
Leu Pro Ala Arg Lys Pro Pro Asn Glu Pro His Val Tyr Leu Pro Gly
         200                 205                 210
```

```
TTA ATA ATT CTG CTT CTC TTC GCG TCT GTG GCC CTG GTG GCT GCC ATC      725
Leu Ile Ile Leu Leu Leu Phe Ala Ser Val Ala Leu Val Ala Ala Ile
    215                 220                 225

ATC TTT GGC GTT TGC TAT AGG AAA AAA GGG AAA GCA CTC ACA GCT AAT      773
Ile Phe Gly Val Cys Tyr Arg Lys Lys Gly Lys Ala Leu Thr Ala Asn
230                 235                 240                 245

TTG TGG CAC TGG ATC AAT GAG GCT TGT GGC CGC CTA AGT GGA GAT AAG      821
Leu Trp His Trp Ile Asn Glu Ala Cys Gly Arg Leu Ser Gly Asp Lys
                250                 255                 260

GAG TCC TCA GGT GAC AGT TGT GTC AGT ACA CAC ACG GCA AAC TTT GGT      869
Glu Ser Ser Gly Asp Ser Cys Val Ser Thr His Thr Ala Asn Phe Gly
            265                 270                 275

CAG CAG GGA GCA TGT GAA GGT GTC TTA CTG CTG ACT CTG GAG GAG AAG      917
Gln Gln Gly Ala Cys Glu Gly Val Leu Leu Leu Thr Leu Glu Glu Lys
        280                 285                 290

ACA TTT CCA GAA GAT ATG TGC TAC CCA GAT CAA GGT GGT GTC TGT CAG      965
Thr Phe Pro Glu Asp Met Cys Tyr Pro Asp Gln Gly Gly Val Cys Gln
    295                 300                 305

GGC ACG TGT GTA GGA GGT GGT CCC TAC GCA CAA GGC GAA GAT GCC AGG     1013
Gly Thr Cys Val Gly Gly Gly Pro Tyr Ala Gln Gly Glu Asp Ala Arg
310                 315                 320                 325

ATG CTC TCA TTG GTC AGC AAG ACC GAG ATA GAG GAA GAC AGC TTC AGA     1061
Met Leu Ser Leu Val Ser Lys Thr Glu Ile Glu Glu Asp Ser Phe Arg
                330                 335                 340

CAG ATG CCC ACA GAA GAT GAA TAC ATG GAC AGG CCC TCC CAG CCC ACA     1109
Gln Met Pro Thr Glu Asp Glu Tyr Met Asp Arg Pro Ser Gln Pro Thr
            345                 350                 355

GAC CAG TTA CTG TTC CTC ACT GAG CCT GGA AGC AAA TCC ACA CCT CCT     1157
Asp Gln Leu Leu Phe Leu Thr Glu Pro Gly Ser Lys Ser Thr Pro Pro
        360                 365                 370

TTC TCT GAA CCC CTG GAG GTG GGG GAG AAT GAC AGT TTA AGC CAG TGC     1205
Phe Ser Glu Pro Leu Glu Val Gly Glu Asn Asp Ser Leu Ser Gln Cys
    375                 380                 385

TTC ACG GGG ACA CAG AGC ACA GTG GGT TCA GAA AGC TGC AAC TGC ACT     1253
Phe Thr Gly Thr Gln Ser Thr Val Gly Ser Glu Ser Cys Asn Cys Thr
390                 395                 400                 405

GAG CCC CTG TGC AGG ACT GAT TGG ACT CCC ATG TCC TCT GAA AAC TAC     1301
Glu Pro Leu Cys Arg Thr Asp Trp Thr Pro Met Ser Ser Glu Asn Tyr
                410                 415                 420

TTG CAA AAA GAG GTG GAC AGT GGC CAT TGC CCG CAC TGG GCA GCC AGC     1349
Leu Gln Lys Glu Val Asp Ser Gly His Cys Pro His Trp Ala Ala Ser
            425                 430                 435

CCC AGC CCC AAC TGG GCA GAT GTC TGC ACA GGC TGC CGG AAC              1391
Pro Ser Pro Asn Trp Ala Asp Val Cys Thr Gly Cys Arg Asn
        440                 445                 450
```

(2) INFORMATION FOR SEQ ID NO:4:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
                20                  25                  30

Pro Cys Thr Ser Glu Lys His Tyr Glu His Leu Gly Arg Cys Cys Asn
            35                  40                  45
```

```
Lys Cys Glu Pro Gly Lys Tyr Met Ser Ser Lys Cys Thr Thr Thr Ser
         50                  55                  60

Asp Ser Val Cys Leu Pro Cys Gly Pro Asp Glu Tyr Leu Asp Ser Trp
 65                  70                  75                  80

Asn Glu Glu Asp Lys Cys Leu Leu His Lys Val Cys Asp Thr Gly Lys
                 85                  90                  95

Ala Leu Val Ala Val Ala Gly Asn Ser Thr Thr Pro Arg Arg Cys
             100                 105                 110

Ala Cys Thr Ala Gly Tyr His Trp Ser Gln Asp Cys Glu Cys Cys Arg
             115                 120                 125

Arg Asn Thr Glu Cys Ala Pro Gly Leu Gly Ala Gln His Pro Leu Gln
         130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                 165                 170                 175

Phe Leu Gly Lys Arg Val Glu His His Gly Thr Glu Lys Ser Asp Ala
             180                 185                 190

Val Cys Ser Ser Ser Leu Pro Ala Arg Lys Pro Pro Asn Glu Pro His
     195                 200                 205

Val Tyr Leu Pro Gly Leu Ile Ile Leu Leu Leu Phe Ala Ser Val Ala
     210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
             245                 250                 255

Leu Ser Gly Asp Lys Glu Ser Ser Gly Asp Ser Cys Val Ser Thr His
             260                 265                 270

Thr Ala Asn Phe Gly Gln Gln Gly Ala Cys Glu Gly Val Leu Leu Leu
         275                 280                 285

Thr Leu Glu Glu Lys Thr Phe Pro Glu Asp Met Cys Tyr Pro Asp Gln
         290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
             325                 330                 335

Glu Asp Ser Phe Arg Gln Met Pro Thr Glu Asp Glu Tyr Met Asp Arg
             340                 345                 350

Pro Ser Gln Pro Thr Asp Gln Leu Leu Phe Leu Thr Glu Pro Gly Ser
         355                 360                 365

Lys Ser Thr Pro Pro Phe Ser Glu Pro Leu Glu Val Gly Glu Asn Asp
     370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
             405                 410                 415

Ser Ser Glu Asn Tyr Leu Gln Lys Glu Val Asp Ser Gly His Cys Pro
             420                 425                 430

His Trp Ala Ala Ser Pro Ser Pro Asn Trp Ala Asp Val Cys Thr Gly
         435                 440                 445

Cys Arg Asn
     450
```

(2) INFORMATION FOR SEQ ID NO:5:

(i) SEQUENCE CHARACTERISTICS:
        (A) LENGTH: 3136 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (vii) IMMEDIATE SOURCE:
        (A) LIBRARY: BONE-MARROW DERIVED DENDRITIC CELLS
        (B) CLONE: FULL LENGTH RANK (ix) FEATURE:
        (A) NAME/KEY: CDS
        (B) LOCATION: 39..1886

(xi) SEQUENCE DESCRIPTION: SEQ ID NO:5:

```
CCGCTGAGGC CGCGGCGCCC GCCAGCCTGT CCCGCGCC ATG GCC CCG CGC GCC         53
                                           Met Ala Pro Arg Ala
                                           1               5

CGG CGG CGC CGC CCG CTG TTC GCG CTG CTG CTG CTC TGC GCG CTG CTC       101
Arg Arg Arg Arg Pro Leu Phe Ala Leu Leu Leu Leu Cys Ala Leu Leu
            10                  15                  20

GCC CGG CTG CAG GTG GCT TTG CAG ATC GCT CCT CCA TGT ACC AGT GAG       149
Ala Arg Leu Gln Val Ala Leu Gln Ile Ala Pro Pro Cys Thr Ser Glu
        25                  30                  35

AAG CAT TAT GAG CAT CTG GGA CGG TGC TGT AAC AAA TGT GAA CCA GGA       197
Lys His Tyr Glu His Leu Gly Arg Cys Cys Asn Lys Cys Glu Pro Gly
    40                  45                  50

AAG TAC ATG TCT TCT AAA TGC ACT ACT ACC TCT GAC AGT GTA TGT CTG       245
Lys Tyr Met Ser Ser Lys Cys Thr Thr Thr Ser Asp Ser Val Cys Leu
55                  60                  65

CCC TGT GGC CCG GAT GAA TAC TTG GAT AGC TGG AAT GAA GAA GAT AAA       293
Pro Cys Gly Pro Asp Glu Tyr Leu Asp Ser Trp Asn Glu Glu Asp Lys
70                  75                  80                  85

TGC TTG CTG CAT AAA GTT TGT GAT ACA GGC AAG GCC CTG GTG GCC GTG       341
Cys Leu Leu His Lys Val Cys Asp Thr Gly Lys Ala Leu Val Ala Val
                90                  95                  100

GTC GCC GGC AAC AGC ACG ACC CCC CGG CGC TGC GCG TGC ACG GCT GGG       389
Val Ala Gly Asn Ser Thr Thr Pro Arg Arg Cys Ala Cys Thr Ala Gly
            105                 110                 115

TAC CAC TGG AGC CAG GAC TGC GAG TGC TGC CGC CGC AAC ACC GAG TGC       437
Tyr His Trp Ser Gln Asp Cys Glu Cys Cys Arg Arg Asn Thr Glu Cys
        120                 125                 130

GCG CCG GGC CTG GGC GCC CAG CAC CCG TTG CAG CTC AAC AAG GAC ACA       485
Ala Pro Gly Leu Gly Ala Gln His Pro Leu Gln Leu Asn Lys Asp Thr
    135                 140                 145

GTG TGC AAA CCT TGC CTT GCA GGC TAC TTC TCT GAT GCC TTT TCC TCC       533
Val Cys Lys Pro Cys Leu Ala Gly Tyr Phe Ser Asp Ala Phe Ser Ser
150                 155                 160                 165

ACG GAC AAA TGC AGA CCC TGG ACC AAC TGT ACC TTC CTT GGA AAG AGA       581
Thr Asp Lys Cys Arg Pro Trp Thr Asn Cys Thr Phe Leu Gly Lys Arg
                170                 175                 180

GTA GAA CAT CAT GGG ACA GAG AAA TCC GAT GCG GTT TGC AGT TCT TCT       629
Val Glu His His Gly Thr Glu Lys Ser Asp Ala Val Cys Ser Ser Ser
            185                 190                 195

CTG CCA GCT AGA AAA CCA CCA AAT GAA CCC CAT GTT TAC TTG CCC GGT       677
```

-continued

```
                Leu Pro Ala Arg Lys Pro Pro Asn Glu Pro His Val Tyr Leu Pro Gly
                                200                 205                 210

TTA ATA ATT CTG CTT CTC TTC GCG TCT GTG GCC CTG GTG GCT GCC ATC              725
Leu Ile Ile Leu Leu Leu Phe Ala Ser Val Ala Leu Val Ala Ala Ile
215                 220                 225

ATC TTT GGC GTT TGC TAT AGG AAA AAA GGG AAA GCA CTC ACA GCT AAT              773
Ile Phe Gly Val Cys Tyr Arg Lys Lys Gly Lys Ala Leu Thr Ala Asn
230                 235                 240                 245

TTG TGG CAC TGG ATC AAT GAG GCT TGT GGC CGC CTA AGT GGA GAT AAG              821
Leu Trp His Trp Ile Asn Glu Ala Cys Gly Arg Leu Ser Gly Asp Lys
                250                 255                 260

GAG TCC TCA GGT GAC AGT TGT GTC AGT ACA CAC ACG GCA AAC TTT GGT              869
Glu Ser Ser Gly Asp Ser Cys Val Ser Thr His Thr Ala Asn Phe Gly
                265                 270                 275

CAG CAG GGA GCA TGT GAA GGT GTC TTA CTG CTG ACT CTG GAG GAG AAG              917
Gln Gln Gly Ala Cys Glu Gly Val Leu Leu Leu Thr Leu Glu Glu Lys
                280                 285                 290

ACA TTT CCA GAA GAT ATG TGC TAC CCA GAT CAA GGT GGT GTC TGT CAG              965
Thr Phe Pro Glu Asp Met Cys Tyr Pro Asp Gln Gly Gly Val Cys Gln
295                 300                 305

GGC ACG TGT GTA GGA GGT GGT CCC TAC GCA CAA GGC GAA GAT GCC AGG             1013
Gly Thr Cys Val Gly Gly Gly Pro Tyr Ala Gln Gly Glu Asp Ala Arg
310                 315                 320                 325

ATG CTC TCA TTG GTC AGC AAG ACC GAG ATA GAG GAA GAC AGC TTC AGA             1061
Met Leu Ser Leu Val Ser Lys Thr Glu Ile Glu Glu Asp Ser Phe Arg
                330                 335                 340

CAG ATG CCC ACA GAA GAT GAA TAC ATG GAC AGG CCC TCC CAG CCC ACA             1109
Gln Met Pro Thr Glu Asp Glu Tyr Met Asp Arg Pro Ser Gln Pro Thr
                345                 350                 355

GAC CAG TTA CTG TTC CTC ACT GAG CCT GGA AGC AAA TCC ACA CCT CCT             1157
Asp Gln Leu Leu Phe Leu Thr Glu Pro Gly Ser Lys Ser Thr Pro Pro
                360                 365                 370

TTC TCT GAA CCC CTG GAG GTG GGG GAG AAT GAC AGT TTA AGC CAG TGC             1205
Phe Ser Glu Pro Leu Glu Val Gly Glu Asn Asp Ser Leu Ser Gln Cys
375                 380                 385

TTC ACG GGG ACA CAG AGC ACA GTG GGT TCA GAA AGC TGC AAC TGC ACT             1253
Phe Thr Gly Thr Gln Ser Thr Val Gly Ser Glu Ser Cys Asn Cys Thr
390                 395                 400                 405

GAG CCC CTG TGC AGG ACT GAT TGG ACT CCC ATG TCC TCT GAA AAC TAC             1301
Glu Pro Leu Cys Arg Thr Asp Trp Thr Pro Met Ser Ser Glu Asn Tyr
                410                 415                 420

TTG CAA AAA GAG GTG GAC AGT GGC CAT TGC CCG CAC TGG GCA GCC AGC             1349
Leu Gln Lys Glu Val Asp Ser Gly His Cys Pro His Trp Ala Ala Ser
                425                 430                 435

CCC AGC CCC AAC TGG GCA GAT GTC TGC ACA GGC TGC CGG AAC CCT CCT             1397
Pro Ser Pro Asn Trp Ala Asp Val Cys Thr Gly Cys Arg Asn Pro Pro
                440                 445                 450

GGG GAG GAC TGT GAA CCC CTC GTG GGT TCC CCA AAA CGT GGA CCC TTG             1445
Gly Glu Asp Cys Glu Pro Leu Val Gly Ser Pro Lys Arg Gly Pro Leu
455                 460                 465

CCC CAG TGC GCC TAT GGC ATG GGC CTT CCC CCT GAA GAA GAA GCC AGC             1493
Pro Gln Cys Ala Tyr Gly Met Gly Leu Pro Pro Glu Glu Glu Ala Ser
470                 475                 480                 485

AGG ACG GAG GCC AGA GAC CAG CCC GAG GAT GGG GCT GAT GGG AGG CTC             1541
Arg Thr Glu Ala Arg Asp Gln Pro Glu Asp Gly Ala Asp Gly Arg Leu
                490                 495                 500

CCA AGC TCA GCG AGG GCA GGT GCC GGG TCT GGA AGC TCC CCT GGT GGC             1589
Pro Ser Ser Ala Arg Ala Gly Ala Gly Ser Gly Ser Ser Pro Gly Gly
                505                 510                 515

CAG TCC CCT GCA TCT GGA AAT GTG ACT GGA AAC AGT AAC TCC ACG TTC             1637
```

```
                Gln Ser Pro Ala Ser Gly Asn Val Thr Gly Asn Ser Asn Ser Thr Phe
                    520                 525                 530

ATC TCC AGC GGG CAG GTG ATG AAC TTC AAG GGC GAC ATC ATC GTG GTC                  1685
Ile Ser Ser Gly Gln Val Met Asn Phe Lys Gly Asp Ile Ile Val Val
    535                 540                 545

TAC GTC AGC CAG ACC TCG CAG GAG GGC GCG GCG GCG GCT GCG GAG CCC                  1733
Tyr Val Ser Gln Thr Ser Gln Glu Gly Ala Ala Ala Ala Ala Glu Pro
550                 555                 560                 565

ATG GGC CGC CCG GTG CAG GAG GAG ACC CTG GCG CGC CGA GAC TCC TTC                  1781
Met Gly Arg Pro Val Gln Glu Glu Thr Leu Ala Arg Arg Asp Ser Phe
                570                 575                 580

GCG GGG AAC GGC CCG CGC TTC CCG GAC CCG TGC GGC GGC CCC GAG GGG                  1829
Ala Gly Asn Gly Pro Arg Phe Pro Asp Pro Cys Gly Gly Pro Glu Gly
            585                 590                 595

CTG CGG GAG CCG GAG AAG GCC TCG AGG CCG GTG CAG GAG CAA GGC GGG                  1877
Leu Arg Glu Pro Glu Lys Ala Ser Arg Pro Val Gln Glu Gln Gly Gly
        600                 605                 610

GCC AAG GCT TGAGCGCCCC CCATGGCTGG GAGCCCGAAG CTCGGAGCCA                          1926
Ala Lys Ala
615

GGGCTCGCGA GGGCAGCACC GCAGCCTCTG CCCCAGCCCC GGCCACCCAG GGATCGATCG                1986

GTACAGTCGA GGAAGACCAC CCGGCATTCT CTGCCCACTT TGCCTTCCAG GAAATGGGCT                2046

TTTCAGGAAG TGAATTGATG AGGACTGTCC CCATGCCCAC GGATGCTCAG CAGCCCGCCG                2106

CACTGGGGCA GATGTCTCCC CTGCCACTCC TCAAACTCGC AGCAGTAATT TGTGGCACTA                2166

TGACAGCTAT TTTTATGACT ATCCTGTTCT GTGGGGGGGG GGTCTATGTT TTCCCCCCAT                2226

ATTTGTATTC CTTTTCATAA CTTTTCTTGA TATCTTTCCT CCCTCTTTTT TAATGTAAAG                2286

GTTTTCTCAA AAATTCTCCT AAAGGTGAGG GTCTCTTTCT TTTCTCTTTT CCTTTTTTTT                2346

TTCTTTTTTT GGCAACCTGG CTCTGGCCCA GGCTAGAGTG CAGTGGTGCG ATTATAGCCC                2406

GGTGCAGCCT CTAACTCCTG GGCTCAAGCA ATCCAAGTGA TCCTCCCACC TCAACCTTCG                2466

GAGTAGCTGG GATCACAGCT GCAGGCCACG CCCAGCTTCC TCCCCCCGAC TCCCCCCCCC                2526

CAGAGACACG GTCCCACCAT GTTACCCAGC CTGGTCTCAA ACTCCCCAGC TAAAGCAGTC                2586

CTCCAGCCTC GGCCTCCCAA AGTACTGGGA TTACAGGCGT GAGCCCCCAC GCTGGCCTGC                2646

TTTACGTATT TTCTTTTGTG CCCCTGCTCA CAGTGTTTTA GAGATGGCTT TCCCAGTGTG                2706

TGTTCATTGT AAACACTTTT GGGAAAGGGC TAAACATGTG AGGCCTGGAG ATAGTTGCTA                2766

AGTTGCTAGG AACATGTGGT GGGACTTTCA TATTCTGAAA AATGTTCTAT ATTCTCATTT                2826

TTCTAAAAGA AAGAAAAAAG GAAACCCGAT TTATTTCTCC TGAATCTTTT TAAGTTTGTG                2886

TCGTTCCTTA AGCAGAACTA AGCTCAGTAT GTGACCTTAC CCGCTAGGTG GTTAATTTAT                2946

CCATGCTGGC AGAGGCACTC AGGTACTTGG TAAGCAAATT TCTAAAACTC CAAGTTGCTG                3006

CAGCTTGGCA TTCTTCTTAT TCTAGAGGTC TCTCTGAAA AGATGGAGAA AATGAACAGG                 3066

ACATGGGGCT CCTGGAAAGA AAGGGCCCGG GAAGTTCAAG GAAGAATAAA GTTGAAATTT                3126

TAAAAAAAAA                                                                       3136

(2) INFORMATION FOR SEQ ID NO:6:

(i) SEQUENCE CHARACTERISTICS:
        (A) LENGTH: 616 amino acids
        (B) TYPE: amino acid
        (D) TOPOLOGY: linear (ii) MOLECULE TYPE: protein (xi) SEQUENCE DESCRIPTION: SEQ ID NO:6:
```

```
Met Ala Pro Arg Ala Arg Arg Arg Pro Leu Phe Ala Leu Leu Leu
 1               5                  10                  15

Leu Cys Ala Leu Leu Ala Arg Leu Gln Val Ala Leu Gln Ile Ala Pro
         20                  25                  30

Pro Cys Thr Ser Glu Lys His Tyr Glu His Leu Gly Arg Cys Cys Asn
             35                  40                  45

Lys Cys Glu Pro Gly Lys Tyr Met Ser Ser Lys Cys Thr Thr Thr Ser
         50                  55                  60

Asp Ser Val Cys Leu Pro Cys Gly Pro Asp Glu Tyr Leu Asp Ser Trp
 65                  70                  75                  80

Asn Glu Glu Asp Lys Cys Leu Leu His Lys Val Cys Asp Thr Gly Lys
                 85                  90                  95

Ala Leu Val Ala Val Val Ala Gly Asn Ser Thr Thr Pro Arg Arg Cys
                100                 105                 110

Ala Cys Thr Ala Gly Tyr His Trp Ser Gln Asp Cys Glu Cys Cys Arg
            115                 120                 125

Arg Asn Thr Glu Cys Ala Pro Gly Leu Gly Ala Gln His Pro Leu Gln
130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Leu Phe Ala Ser Val Ala
210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
        355                 360                 365

Lys Ser Thr Pro Pro Phe Ser Glu Pro Leu Glu Val Gly Glu Asn Asp
370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
```

-continued

```
                420                 425                 430
    His Trp Ala Ala Ser Pro Ser Pro Asn Trp Ala Asp Val Cys Thr Gly
                    435                 440                 445
    Cys Arg Asn Pro Pro Gly Glu Asp Cys Glu Pro Leu Val Gly Ser Pro
        450                 455                 460
    Lys Arg Gly Pro Leu Pro Gln Cys Ala Tyr Gly Met Gly Leu Pro Pro
    465                 470                 475                 480
    Glu Glu Glu Ala Ser Arg Thr Glu Ala Arg Asp Gln Pro Glu Asp Gly
                        485                 490                 495
    Ala Asp Gly Arg Leu Pro Ser Ser Ala Arg Ala Gly Ala Gly Ser Gly
                    500                 505                 510
    Ser Ser Pro Gly Gly Gln Ser Pro Ala Ser Gly Asn Val Thr Gly Asn
                515                 520                 525
    Ser Asn Ser Thr Phe Ile Ser Ser Gly Gln Val Met Asn Phe Lys Gly
            530                 535                 540
    Asp Ile Ile Val Val Tyr Val Ser Gln Thr Ser Gln Glu Gly Ala Ala
    545                 550                 555                 560
    Ala Ala Ala Glu Pro Met Gly Arg Pro Val Gln Glu Glu Thr Leu Ala
                    565                 570                 575
    Arg Arg Asp Ser Phe Ala Gly Asn Gly Pro Arg Phe Pro Asp Pro Cys
                580                 585                 590
    Gly Gly Pro Glu Gly Leu Arg Glu Pro Glu Lys Ala Ser Arg Pro Val
            595                 600                 605
    Gln Glu Gln Gly Gly Ala Lys Ala
        610                 615

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: FLAG_ peptide (xi) SEQUENCE DESCRIPTION: SEQ ID NO:7:

Asp Tyr Lys Asp Asp Asp Asp Lys
1               5

(2) INFORMATION FOR SEQ ID NO:8:

(i) SEQUENCE CHARACTERISTICS:
        (A) LENGTH: 232 amino acids
        (B) TYPE: amino acid
        (C) STRANDEDNESS: Not Relevant
        (D) TOPOLOGY: linear (ii) MOLECULE TYPE: protein (vi) ORIGINAL SOURCE:
        (A) ORGANISM: Human (vii) IMMEDIATE SOURCE:
        (B) CLONE: IgG1 Fc mutein (xi) SEQUENCE DESCRIPTION: SEQ ID NO:8:

Glu Pro Arg Ser Cys Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
```

-continued

```
                20                  25                  30
Lys Asp Thr Leu Met Ile Ser Arg Thr Pro Glu Val Thr Cys Val Val
            35                  40                  45
Val Asp Val Ser His Glu Asp Pro Glu Val Lys Phe Asn Trp Tyr Val
 50                  55                  60
Asp Gly Val Glu Val His Asn Ala Lys Thr Lys Pro Arg Glu Glu Gln
 65                  70                  75                  80
Tyr Asn Ser Thr Tyr Arg Val Val Ser Val Leu Thr Val Leu His Gln
                85                  90                  95
Asp Trp Leu Asn Gly Lys Asp Tyr Lys Cys Lys Val Ser Asn Lys Ala
                100                 105                 110
Leu Pro Ala Pro Met Gln Lys Thr Ile Ser Lys Ala Lys Gly Gln Pro
            115                 120                 125
Arg Glu Pro Gln Val Tyr Thr Leu Pro Pro Ser Arg Asp Glu Leu Thr
130                 135                 140
Lys Asn Gln Val Ser Leu Thr Cys Leu Val Lys Gly Phe Tyr Pro Arg
145                 150                 155                 160
His Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230

(2) INFORMATION FOR SEQ ID NO:9:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (vi) ORIGINAL SOURCE:
         (A) ORGANISM: CMV (R2780 Leader)

(ix) FEATURE:
         (D) OTHER INFORMATION: Met1-Arg28 is the actual leader
             peptide; Arg29 strengthens the furin cleavage site;
             nucleotides encoding eThr30 and Ser31 add a SpeI site.

(xi) SEQUENCE DESCRIPTION: SEQ ID NO:9:

Met Ala Arg Arg Leu Trp Ile Leu Ser Leu Leu Ala Val Thr Leu Thr
1               5                   10                  15
Val Ala Leu Ala Ala Pro Ser Gln Lys Ser Lys Arg Arg Thr Ser
            20                  25                  30

(2) INFORMATION FOR SEQ ID NO:10:

(i) SEQUENCE CHARACTERISTICS:
        (A) LENGTH: 1630 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (vi) ORIGINAL SOURCE:
     (A) ORGANISM: Mus musculus (vii) IMMEDIATE SOURCE:
      (A) LIBRARY:
      (B) CLONE: RANKL (ix) FEATURE:
     (A) NAME/KEY: CDS
     (B) LOCATION: 3..884

(xi) SEQUENCE DESCRIPTION: SEQ ID NO:10:

```
CC GGC GTC CCA CAC GAG GGT CCG CTG CAC CCC GCG CCT TCT GCA CCG          47
   Gly Val Pro His Glu Gly Pro Leu His Pro Ala Pro Ser Ala Pro
    1               5                  10                  15

GCT CCG GCG CCG CCA CCC GCC GCC TCC CGC TCC ATG TTC CTG GCC CTC          95
Ala Pro Ala Pro Pro Pro Ala Ala Ser Arg Ser Met Phe Leu Ala Leu
                 20                  25                  30

CTG GGG CTG GGA CTG GGC CAG GTG GTC TGC AGC ATC GCT CTG TTC CTG         143
Leu Gly Leu Gly Leu Gly Gln Val Val Cys Ser Ile Ala Leu Phe Leu
                35                  40                  45

TAC TTT CGA GCG CAG ATG GAT CCT AAC AGA ATA TCA GAA GAC AGC ACT         191
Tyr Phe Arg Ala Gln Met Asp Pro Asn Arg Ile Ser Glu Asp Ser Thr
         50                  55                  60

CAC TGC TTT TAT AGA ATC CTG AGA CTC CAT GAA AAC GCA GAT TTG CAG         239
His Cys Phe Tyr Arg Ile Leu Arg Leu His Glu Asn Ala Asp Leu Gln
 65                  70                  75

GAC TCG ACT CTG GAG AGT GAA GAC ACA CTA CCT GAC TCC TGC AGG AGG         287
Asp Ser Thr Leu Glu Ser Glu Asp Thr Leu Pro Asp Ser Cys Arg Arg
 80                  85                  90                  95

ATG AAA CAA GCC TTT CAG GGG GCC GTG CAG AAG GAA CTG CAA CAC ATT         335
Met Lys Gln Ala Phe Gln Gly Ala Val Gln Lys Glu Leu Gln His Ile
                100                 105                 110

GTG GGG CCA CAG CGC TTC TCA GGA GCT CCA GCT ATG ATG GAA GGC TCA         383
Val Gly Pro Gln Arg Phe Ser Gly Ala Pro Ala Met Met Glu Gly Ser
            115                 120                 125

TGG TTG GAT GTG GCC CAG CGA GGC AAG CCT GAG GCC CAG CCA TTT GCA         431
Trp Leu Asp Val Ala Gln Arg Gly Lys Pro Glu Ala Gln Pro Phe Ala
        130                 135                 140

CAC CTC ACC ATC AAT GCT GCC AGC ATC CCA TCG GGT TCC CAT AAA GTC         479
His Leu Thr Ile Asn Ala Ala Ser Ile Pro Ser Gly Ser His Lys Val
    145                 150                 155

ACT CTG TCC TCT TGG TAC CAC GAT CGA GGC TGG GCC AAG ATC TCT AAC         527
Thr Leu Ser Ser Trp Tyr His Asp Arg Gly Trp Ala Lys Ile Ser Asn
160                 165                 170                 175

ATG ACG TTA AGC AAC GGA AAA CTA AGG GTT AAC CAA GAT GGC TTC TAT         575
Met Thr Leu Ser Asn Gly Lys Leu Arg Val Asn Gln Asp Gly Phe Tyr
                180                 185                 190

TAC CTG TAC GCC AAC ATT TGC TTT CGG CAT CAT GAA ACA TCG GGA AGC         623
Tyr Leu Tyr Ala Asn Ile Cys Phe Arg His His Glu Thr Ser Gly Ser
            195                 200                 205

GTA CCT ACA GAC TAT CTT CAG CTG ATG GTG TAT GTC GTT AAA ACC AGC         671
Val Pro Thr Asp Tyr Leu Gln Leu Met Val Tyr Val Val Lys Thr Ser
        210                 215                 220

ATC AAA ATC CCA AGT TCT CAT AAC CTG ATG AAA GGA GGG AGC ACG AAA         719
Ile Lys Ile Pro Ser Ser His Asn Leu Met Lys Gly Gly Ser Thr Lys
    225                 230                 235
```

```
AAC TGG TCG GGC AAT TCT GAA TTC CAC TTT TAT TCC ATA AAT GTT GGG      767
Asn Trp Ser Gly Asn Ser Glu Phe His Phe Tyr Ser Ile Asn Val Gly
240                 245                 250                 255

GGA TTT TTC AAG CTC CGA GCT GGT GAA GAA ATT AGC ATT CAG GTG TCC      815
Gly Phe Phe Lys Leu Arg Ala Gly Glu Glu Ile Ser Ile Gln Val Ser
                260                 265                 270

AAC CCT TCC CTG CTG GAT CCG GAT CAA GAT GCG ACG TAC TTT GGG GCT      863
Asn Pro Ser Leu Leu Asp Pro Asp Gln Asp Ala Thr Tyr Phe Gly Ala
            275                 280                 285

TTC AAA GTT CAG GAC ATA GAC TGAGACTCAT TCGTGGAAC ATTAGCATGG          914
Phe Lys Val Gln Asp Ile Asp
        290

ATGTCCTAGA TGTTTGGAAA CTTCTTAAAA AATGGATGAT GTCTATACAT GTGTAAGACT    974

ACTAAGAGAC ATGGCCCACG GTGTATGAAA CTCACAGCCC TCTCTCTTGA GCCTGTACAG   1034

GTTGTGTATA TGTAAAGTCC ATAGGTGATG TTAGATTCAT GGTGATTACA CAACGGTTTT   1094

ACAATTTTGT AATGATTTCC TAGAATTGAA CCAGATTGGG AGAGGTATTC CGATGCTTAT   1154

GAAAAACTTA CACGTGAGCT ATGGAAGGGG GTCACAGTCT CTGGGTCTAA CCCCTGGACA   1214

TGTGCCACTG AGAACCTTGA AATTAAGAGG ATGCCATGTC ATTGCAAAGA ATGATAGTG    1274

TGAAGGGTTA AGTTCTTTTG AATTGTTACA TTGCGCTGGG ACCTGCAAAT AAGTTCTTTT   1334

TTTCTAATGA GGAGAGAAAA ATATATGTAT TTTTATATAA TGTCTAAAGT TATATTTCAG   1394

GTGTAATGTT TTCTGTGCAA AGTTTTGTAA ATTATATTTG TGCTATAGTA TTTGATTCAA   1454

AATATTTAAA AATGTCTCAC TGTTGACATA TTTAATGTTT TAAATGTACA GATGTATTTA   1514

ACTGGTGCAC TTTGTAATTC CCCTGAAGGT ACTCGTAGCT AAGGGGGCAG AATACTGTTT   1574

CTGGTGACCA CATGTAGTTT ATTTCTTTAT TCTTTTTAAC TTAATAGAGT CTTCAG       1630

(2) INFORMATION FOR SEQ ID NO:11:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO:11:

Gly Val Pro His Glu Gly Pro Leu His Pro Ala Pro Ser Ala Pro Ala
1               5                   10                  15

Pro Ala Pro Pro Ala Ala Ser Arg Ser Met Phe Leu Ala Leu Leu
            20                  25                  30

Gly Leu Gly Leu Gly Gln Val Val Cys Ser Ile Ala Leu Phe Leu Tyr
        35                  40                  45

Phe Arg Ala Gln Met Asp Pro Asn Arg Ile Ser Glu Asp Ser Thr His
    50                  55                  60

Cys Phe Tyr Arg Ile Leu Arg Leu His Glu Asn Ala Asp Leu Gln Asp
65                  70                  75                  80

Ser Thr Leu Glu Ser Glu Asp Thr Leu Pro Asp Ser Cys Arg Arg Met
                85                  90                  95

Lys Gln Ala Phe Gln Gly Ala Val Gln Lys Glu Leu Gln His Ile Val
            100                 105                 110

Gly Pro Gln Arg Phe Ser Gly Ala Pro Ala Met Met Glu Gly Ser Trp
        115                 120                 125

Leu Asp Val Ala Gln Arg Gly Lys Pro Glu Ala Gln Pro Phe Ala His
    130                 135                 140

Leu Thr Ile Asn Ala Ala Ser Ile Pro Ser Gly Ser His Lys Val Thr
```

145 150 155 160
Leu Ser Ser Trp Tyr His Asp Arg Gly Trp Ala Lys Ile Ser Asn Met
              165                 170                 175

Thr Leu Ser Asn Gly Lys Leu Arg Val Asn Gln Asp Gly Phe Tyr Tyr
          180                 185                 190

Leu Tyr Ala Asn Ile Cys Phe Arg His His Glu Thr Ser Gly Ser Val
      195                 200                 205

Pro Thr Asp Tyr Leu Gln Leu Met Val Tyr Val Lys Thr Ser Ile
  210                 215                 220

Lys Ile Pro Ser Ser His Asn Leu Met Lys Gly Gly Ser Thr Lys Asn
225                 230                 235                 240

Trp Ser Gly Asn Ser Glu Phe His Phe Tyr Ser Ile Asn Val Gly Gly
              245                 250                 255

Phe Phe Lys Leu Arg Ala Gly Glu Glu Ile Ser Ile Gln Val Ser Asn
          260                 265                 270

Pro Ser Leu Leu Asp Pro Asp Gln Asp Ala Thr Tyr Phe Gly Ala Phe
          275                 280                 285

Lys Val Gln Asp Ile Asp
      290

(2) INFORMATION FOR SEQ ID NO:12:

(i) SEQUENCE CHARACTERISTICS:
        (A) LENGTH: 954 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (A) LIBRARY:
        (B) CLONE: huRANKL (full length)

(ix) FEATURE:
        (A) NAME/KEY: CDS
        (B) LOCATION: 1..951

(xi) SEQUENCE DESCRIPTION: SEQ ID NO:12:

ATG CGC CGC GCC AGC AGA GAC TAC ACC AAG TAC CTG CGT GGC TCG GAG     48
Met Arg Arg Ala Ser Arg Asp Tyr Thr Lys Tyr Leu Arg Gly Ser Glu
 1               5                  10                  15

GAG ATG GGC GGC GGC CCC GGA GCC CCG CAC GAG GGC CCC CTG CAC GCC     96
Glu Met Gly Gly Gly Pro Gly Ala Pro His Glu Gly Pro Leu His Ala
             20                  25                  30

CCG CCG CCG CCT GCG CCG CAC CAG CCC CCC GCC GCC TCC CGC TCC ATG    144
Pro Pro Pro Pro Ala Pro His Gln Pro Pro Ala Ala Ser Arg Ser Met
         35                  40                  45

TTC GTG GCC CTC CTG GGG CTG GGG CTG GGC CAG GTT GTC TGC AGC GTC    192
Phe Val Ala Leu Leu Gly Leu Gly Leu Gly Gln Val Val Cys Ser Val
     50                  55                  60

GCC CTG TTC TTC TAT TTC AGA GCG CAG ATG GAT CCT AAT AGA ATA TCA    240
Ala Leu Phe Phe Tyr Phe Arg Ala Gln Met Asp Pro Asn Arg Ile Ser
 65                  70                  75                  80

GAA GAT GGC ACT CAC TGC ATT TAT AGA ATT TTG AGA CTC CAT GAA AAT    288
Glu Asp Gly Thr His Cys Ile Tyr Arg Ile Leu Arg Leu His Glu Asn
                 85                  90                  95

```
GCA GAT TTT CAA GAC ACA ACT CTG GAG AGT CAA GAT ACA AAA TTA ATA        336
Ala Asp Phe Gln Asp Thr Thr Leu Glu Ser Gln Asp Thr Lys Leu Ile
            100                 105                 110

CCT GAT TCA TGT AGG AGA ATT AAA CAG GCC TTT CAA GGA GCT GTG CAA        384
Pro Asp Ser Cys Arg Arg Ile Lys Gln Ala Phe Gln Gly Ala Val Gln
            115                 120                 125

AAG GAA TTA CAA CAT ATC GTT GGA TCA CAG CAC ATC AGA GCA GAG AAA        432
Lys Glu Leu Gln His Ile Val Gly Ser Gln His Ile Arg Ala Glu Lys
    130                 135                 140

GCG ATG GTG GAT GGC TCA TGG TTA GAT CTG GCC AAG AGG AGC AAG CTT        480
Ala Met Val Asp Gly Ser Trp Leu Asp Leu Ala Lys Arg Ser Lys Leu
145                 150                 155                 160

GAA GCT CAG CCT TTT GCT CAT CTC ACT ATT AAT GCC ACC GAC ATC CCA        528
Glu Ala Gln Pro Phe Ala His Leu Thr Ile Asn Ala Thr Asp Ile Pro
                165                 170                 175

TCT GGT TCC CAT AAA GTG AGT CTG TCC TCT TGG TAC CAT GAT CGG GGT        576
Ser Gly Ser His Lys Val Ser Leu Ser Ser Trp Tyr His Asp Arg Gly
            180                 185                 190

TGG GCC AAG ATC TCC AAC ATG ACT TTT AGC AAT GGA AAA CTA ATA GTT        624
Trp Ala Lys Ile Ser Asn Met Thr Phe Ser Asn Gly Lys Leu Ile Val
            195                 200                 205

AAT CAG GAT GGC TTT TAT TAC CTG TAT GCC AAC ATT TGC TTT CGA CAT        672
Asn Gln Asp Gly Phe Tyr Tyr Leu Tyr Ala Asn Ile Cys Phe Arg His
    210                 215                 220

CAT GAA ACT TCA GGA GAC CTA GCT ACA GAG TAT CTT CAA CTA ATG GTG        720
His Glu Thr Ser Gly Asp Leu Ala Thr Glu Tyr Leu Gln Leu Met Val
225                 230                 235                 240

TAC GTC ACT AAA ACC AGC ATC AAA ATC CCA AGT TCT CAT ACC CTG ATG        768
Tyr Val Thr Lys Thr Ser Ile Lys Ile Pro Ser Ser His Thr Leu Met
                245                 250                 255

AAA GGA GGA AGC ACC AAG TAT TGG TCA GGG AAT TCT GAA TTC CAT TTT        816
Lys Gly Gly Ser Thr Lys Tyr Trp Ser Gly Asn Ser Glu Phe His Phe
            260                 265                 270

TAT TCC ATA AAC GTT GGT GGA TTT TTT AAG TTA CGG TCT GGA GAG GAA        864
Tyr Ser Ile Asn Val Gly Gly Phe Phe Lys Leu Arg Ser Gly Glu Glu
            275                 280                 285

ATC AGC ATC GAG GTC TCC AAC CCC TCC TTA CTG GAT CCG GAT CAG GAT        912
Ile Ser Ile Glu Val Ser Asn Pro Ser Leu Leu Asp Pro Asp Gln Asp
    290                 295                 300

GCA ACA TAC TTT GGG GCT TTT AAA GTT CGA GAT ATA GAT TGA                954
Ala Thr Tyr Phe Gly Ala Phe Lys Val Arg Asp Ile Asp
305                 310                 315
```

(2) INFORMATION FOR SEQ ID NO:13:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:13:

```
Met Arg Arg Ala Ser Arg Asp Tyr Thr Lys Tyr Leu Arg Gly Ser Glu
 1               5                  10                  15

Glu Met Gly Gly Gly Pro Gly Ala Pro His Glu Gly Pro Leu His Ala
                20                  25                  30

Pro Pro Pro Ala Pro His Gln Pro Pro Ala Ala Ser Arg Ser Met
            35                  40                  45

Phe Val Ala Leu Leu Gly Leu Gly Leu Gly Gln Val Val Cys Ser Val
        50                  55                  60
```

```
Ala Leu Phe Phe Tyr Phe Arg Ala Gln Met Asp Pro Asn Arg Ile Ser
 65                  70                  75                  80

Glu Asp Gly Thr His Cys Ile Tyr Arg Ile Leu Arg Leu His Glu Asn
                 85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315

(2) INFORMATION FOR SEQ ID NO:14:

(i) SEQUENCE CHARACTERISTICS:
        (A) LENGTH: 1878 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Murine (vii) IMMEDIATE SOURCE:
        (A) LIBRARY: Murine Fetal Liver Epithelium
        (B) CLONE: muRANK (ix) FEATURE:
        (A) NAME/KEY: CDS
        (B) LOCATION: 1..1875

(xi) SEQUENCE DESCRIPTION: SEQ ID NO:14:

ATG GCC CCG CGC GCC CGG CGG CGC CGC CAG CTG CCC GCG CCG CTG CTG      48
Met Ala Pro Arg Ala Arg Arg Arg Arg Gln Leu Pro Ala Pro Leu Leu
 1               5                  10                  15
```

```
GCG CTC TGC GTG CTG CTC GTT CCA CTG CAG GTG ACT CTC CAG GTC ACT        96
Ala Leu Cys Val Leu Leu Val Pro Leu Gln Val Thr Leu Gln Val Thr
         20                  25                  30

CCT CCA TGC ACC CAG GAG AGG CAT TAT GAG CAT CTC GGA CGG TGT TGC       144
Pro Pro Cys Thr Gln Glu Arg His Tyr Glu His Leu Gly Arg Cys Cys
         35                  40                  45

AGC AGA TGC GAA CCA GGA AAG TAC CTG TCC TCT AAG TGC ACT CCT ACC       192
Ser Arg Cys Glu Pro Gly Lys Tyr Leu Ser Ser Lys Cys Thr Pro Thr
 50                  55                  60

TCC GAC AGT GTG TGT CTG CCC TGT GGC CCC GAT GAG TAC TTG GAC ACC       240
Ser Asp Ser Val Cys Leu Pro Cys Gly Pro Asp Glu Tyr Leu Asp Thr
 65                  70                  75                  80

TGG AAT GAA GAA GAT AAA TGC TTG CTG CAT AAA GTC TGT GAT GCA GGC       288
Trp Asn Glu Glu Asp Lys Cys Leu Leu His Lys Val Cys Asp Ala Gly
                 85                  90                  95

AAG GCC CTG GTG GCG GTG GAT CCT GGC AAC CAC ACG GCC CCG CGT CGC       336
Lys Ala Leu Val Ala Val Asp Pro Gly Asn His Thr Ala Pro Arg Arg
                100                 105                 110

TGT GCT TGC ACG GCT GGC TAC CAC TGG AAC TCA GAC TGC GAG TGC TGC       384
Cys Ala Cys Thr Ala Gly Tyr His Trp Asn Ser Asp Cys Glu Cys Cys
            115                 120                 125

CGC AGG AAC ACG GAG TGT GCA CCT GGC TTC GGA GCT CAG CAT CCC TTG       432
Arg Arg Asn Thr Glu Cys Ala Pro Gly Phe Gly Ala Gln His Pro Leu
130                 135                 140

CAG CTC AAC AAG GAT ACG GTG TGC ACA CCC TGC CTC CTG GGC TTC TTC       480
Gln Leu Asn Lys Asp Thr Val Cys Thr Pro Cys Leu Leu Gly Phe Phe
145                 150                 155                 160

TCA GAT GTC TTT TCG TCC ACA GAC AAA TGC AAA CCT TGG ACC AAC TGC       528
Ser Asp Val Phe Ser Ser Thr Asp Lys Cys Lys Pro Trp Thr Asn Cys
                165                 170                 175

ACC CTC CTT GGA AAG CTA GAA GCA CAC CAG GGG ACA ACG GAA TCA GAT       576
Thr Leu Leu Gly Lys Leu Glu Ala His Gln Gly Thr Thr Glu Ser Asp
            180                 185                 190

GTG GTC TGC AGC TCT TCC ATG ACA CTG AGG AGA CCA CCC AAG GAG GCC       624
Val Val Cys Ser Ser Ser Met Thr Leu Arg Arg Pro Pro Lys Glu Ala
        195                 200                 205

CAG GCT TAC CTG CCC AGT CTC ATC GTT CTG CTC CTC TTC ATC TCT GTG       672
Gln Ala Tyr Leu Pro Ser Leu Ile Val Leu Leu Leu Phe Ile Ser Val
210                 215                 220

GTA GTA GTG GCT GCC ATC ATC TTC GGC GTT TAC TAC AGG AAG GGA GGG       720
Val Val Val Ala Ala Ile Ile Phe Gly Val Tyr Tyr Arg Lys Gly Gly
225                 230                 235                 240

AAA GCG CTG ACA GCT AAT TTG TGG AAT TGG GTC AAT GAT GCT TGC AGT       768
Lys Ala Leu Thr Ala Asn Leu Trp Asn Trp Val Asn Asp Ala Cys Ser
                245                 250                 255

AGT CTA AGT GGA AAT AAG GAG TCC TCA GGG GAC CGT TGT GCT GGT TCC       816
Ser Leu Ser Gly Asn Lys Glu Ser Ser Gly Asp Arg Cys Ala Gly Ser
            260                 265                 270

CAC TCG GCA ACC TCC AGT CAG CAA GAA GTG TGT GAA GGT ATC TTA CTA       864
His Ser Ala Thr Ser Ser Gln Gln Glu Val Cys Glu Gly Ile Leu Leu
        275                 280                 285

ATG ACT CGG GAG GAG AAG ATG GTT CCA GAA GAC GGT GCT GGA GTC TGT       912
Met Thr Arg Glu Glu Lys Met Val Pro Glu Asp Gly Ala Gly Val Cys
290                 295                 300

GGG CCT GTG TGT GCG GCA GGT GGG CCC TGG GCA GAA GTC AGA GAT TCT       960
Gly Pro Val Cys Ala Ala Gly Gly Pro Trp Ala Glu Val Arg Asp Ser
305                 310                 315                 320

AGG ACG TTC ACA CTG GTC AGC GAG GTT GAG ACG CAA GGA GAC CTC TCG      1008
Arg Thr Phe Thr Leu Val Ser Glu Val Glu Thr Gln Gly Asp Leu Ser
                325                 330                 335
```

```
AGG AAG ATT CCC ACA GAG GAT GAG TAC ACG GAC CGG CCC TCG CAG CCT        1056
Arg Lys Ile Pro Thr Glu Asp Glu Tyr Thr Asp Arg Pro Ser Gln Pro
            340                 345                 350

TCG ACT GGT TCA CTG CTC CTA ATC CAG CAG GGA AGC AAA TCT ATA CCC        1104
Ser Thr Gly Ser Leu Leu Leu Ile Gln Gln Gly Ser Lys Ser Ile Pro
            355                 360                 365

CCA TTC CAG GAG CCC CTG GAA GTG GGG GAG AAC GAC AGT TTA AGC CAG        1152
Pro Phe Gln Glu Pro Leu Glu Val Gly Glu Asn Asp Ser Leu Ser Gln
            370                 375                 380

TGT TTC ACC GGG ACT GAA AGC ACG GTG GAT TCT GAG GGC TGT GAC TTC        1200
Cys Phe Thr Gly Thr Glu Ser Thr Val Asp Ser Glu Gly Cys Asp Phe
385                 390                 395                 400

ACT GAG CCT CCG AGC AGA ACT GAC TCT ATG CCC GTG TCC CCT GAA AAG        1248
Thr Glu Pro Pro Ser Arg Thr Asp Ser Met Pro Val Ser Pro Glu Lys
            405                 410                 415

CAC CTG ACA AAA GAA ATA GAA GGT GAC AGT TGC CTC CCC TGG GTG GTC        1296
His Leu Thr Lys Glu Ile Glu Gly Asp Ser Cys Leu Pro Trp Val Val
            420                 425                 430

AGC TCC AAC TCA ACA GAT GGC TAC ACA GGC AGT GGG AAC ACT CCT GGG        1344
Ser Ser Asn Ser Thr Asp Gly Tyr Thr Gly Ser Gly Asn Thr Pro Gly
            435                 440                 445

GAG GAC CAT GAA CCC TTT CCA GGG TCC CTG AAA TGT GGA CCA TTG CCC        1392
Glu Asp His Glu Pro Phe Pro Gly Ser Leu Lys Cys Gly Pro Leu Pro
            450                 455                 460

CAG TGT GCC TAC AGC ATG GGC TTT CCC AGT GAA GCA GCA GCC AGC ATG        1440
Gln Cys Ala Tyr Ser Met Gly Phe Pro Ser Glu Ala Ala Ala Ser Met
465                 470                 475                 480

GCA GAG GCG GGA GTA CGG CCC CAG GAC AGG GCT GAT GAG AGG GGA GCC        1488
Ala Glu Ala Gly Val Arg Pro Gln Asp Arg Ala Asp Glu Arg Gly Ala
            485                 490                 495

TCA GGG TCC GGG AGC TCC CCC AGT GAC CAG CCA CCT GCC TCT GGG AAC        1536
Ser Gly Ser Gly Ser Ser Pro Ser Asp Gln Pro Pro Ala Ser Gly Asn
            500                 505                 510

GTG ACT GGA AAC AGT AAC TCC ACG TTC ATC TCT AGC GGG CAG GTG ATG        1584
Val Thr Gly Asn Ser Asn Ser Thr Phe Ile Ser Ser Gly Gln Val Met
            515                 520                 525

AAC TTC AAG GGT GAC ATC ATC GTG GTG TAT GTC AGC CAG ACC TCG CAG        1632
Asn Phe Lys Gly Asp Ile Ile Val Val Tyr Val Ser Gln Thr Ser Gln
            530                 535                 540

GAG GGC CCG GGT TCC GCA GAG CCC GAG TCG GAG CCC GTG GGC CGC CCT        1680
Glu Gly Pro Gly Ser Ala Glu Pro Glu Ser Glu Pro Val Gly Arg Pro
545                 550                 555                 560

GTG CAG GAG GAG ACG CTG GCA CAC AGA GAC TCC TTT GCG GGC ACC GCG        1728
Val Gln Glu Glu Thr Leu Ala His Arg Asp Ser Phe Ala Gly Thr Ala
            565                 570                 575

CCG CGC TTC CCC GAC GTC TGT GCC ACC GGG GCT GGG CTG CAG GAG CAG        1776
Pro Arg Phe Pro Asp Val Cys Ala Thr Gly Ala Gly Leu Gln Glu Gln
            580                 585                 590

GGG GCA CCC CGG CAG AAG GAC GGG ACA TCG CGG CCG GTG CAG GAG CAG        1824
Gly Ala Pro Arg Gln Lys Asp Gly Thr Ser Arg Pro Val Gln Glu Gln
            595                 600                 605

GGT GGG GCG CAG ACT TCA CTC CAT ACC CAG GGG TCC GGA CAA TGT GCA        1872
Gly Gly Ala Gln Thr Ser Leu His Thr Gln Gly Ser Gly Gln Cys Ala
            610                 615                 620

GAA TGA                                                                1878
Glu
625
```

(2) INFORMATION FOR SEQ ID NO:15:

```
    (i) SEQUENCE CHARACTERISTICS:
        (A) LENGTH: 625 amino acids
        (B) TYPE: amino acid
        (D) TOPOLOGY: linear (ii) MOLECULE TYPE: protein (xi) SEQUENCE DESCRIPTION: SEQ ID NO:15:

Met Ala Pro Arg Ala Arg Arg Arg Gln Leu Pro Ala Pro Leu Leu
 1               5                  10                  15

Ala Leu Cys Val Leu Val Pro Leu Gln Val Thr Leu Gln Val Thr
                20                  25                  30

Pro Pro Cys Thr Gln Glu Arg His Tyr Glu His Leu Gly Arg Cys Cys
            35                  40                  45

Ser Arg Cys Glu Pro Gly Lys Tyr Leu Ser Ser Lys Cys Thr Pro Thr
    50                  55                  60

Ser Asp Ser Val Cys Leu Pro Cys Gly Pro Asp Glu Tyr Leu Asp Thr
 65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro Arg Arg
                100                 105                 110

Cys Ala Cys Thr Ala Gly Tyr His Trp Asn Ser Asp Cys Glu Cys Cys
            115                 120                 125

Arg Arg Asn Thr Glu Cys Ala Pro Gly Phe Gly Ala Gln His Pro Leu
130                 135                 140

Gln Leu Asn Lys Asp Thr Val Cys Thr Pro Cys Leu Leu Gly Phe Phe
145                 150                 155                 160

Ser Asp Val Phe Ser Ser Thr Asp Lys Cys Lys Pro Trp Thr Asn Cys
                165                 170                 175

Thr Leu Leu Gly Lys Leu Glu Ala His Gln Gly Thr Thr Glu Ser Asp
                180                 185                 190

Val Val Cys Ser Ser Ser Met Thr Leu Arg Arg Pro Lys Glu Ala
                195                 200                 205

Gln Ala Tyr Leu Pro Ser Leu Ile Val Leu Leu Phe Ile Ser Val
    210                 215                 220

Val Val Val Ala Ala Ile Ile Phe Gly Val Tyr Tyr Arg Lys Gly Gly
225                 230                 235                 240

Lys Ala Leu Thr Ala Asn Leu Trp Asn Trp Val Asn Asp Ala Cys Ser
                245                 250                 255

Ser Leu Ser Gly Asn Lys Glu Ser Ser Gly Asp Arg Cys Ala Gly Ser
                260                 265                 270

His Ser Ala Thr Ser Ser Gln Gln Glu Val Cys Glu Gly Ile Leu Leu
    275                 280                 285

Met Thr Arg Glu Glu Lys Met Val Pro Glu Asp Gly Ala Gly Val Cys
290                 295                 300

Gly Pro Val Cys Ala Ala Gly Gly Pro Trp Ala Glu Val Arg Asp Ser
305                 310                 315                 320

Arg Thr Phe Thr Leu Val Ser Glu Val Glu Thr Gln Gly Asp Leu Ser
                325                 330                 335

Arg Lys Ile Pro Thr Glu Asp Glu Tyr Thr Asp Arg Pro Ser Gln Pro
                340                 345                 350

Ser Thr Gly Ser Leu Leu Leu Ile Gln Gln Gly Ser Lys Ser Ile Pro
                355                 360                 365

Pro Phe Gln Glu Pro Leu Glu Val Gly Glu Asn Asp Ser Leu Ser Gln
                370                 375                 380
```

-continued

```
Cys Phe Thr Gly Thr Glu Ser Thr Val Asp Ser Glu Gly Cys Asp Phe
385                 390                 395                 400

Thr Glu Pro Pro Ser Arg Thr Asp Ser Met Pro Val Ser Pro Glu Lys
            405                 410                 415

His Leu Thr Lys Glu Ile Glu Gly Asp Ser Cys Leu Pro Trp Val Val
            420                 425                 430

Ser Ser Asn Ser Thr Asp Gly Tyr Thr Gly Ser Gly Asn Thr Pro Gly
            435                 440                 445

Glu Asp His Glu Pro Phe Pro Gly Ser Leu Lys Cys Gly Pro Leu Pro
450                 455                 460

Gln Cys Ala Tyr Ser Met Gly Phe Pro Ser Glu Ala Ala Ser Met
465                 470                 475                 480

Ala Glu Ala Gly Val Arg Pro Gln Asp Arg Ala Asp Glu Arg Gly Ala
                485                 490                 495

Ser Gly Ser Gly Ser Ser Pro Ser Asp Gln Pro Pro Ala Ser Gly Asn
                500                 505                 510

Val Thr Gly Asn Ser Asn Ser Thr Phe Ile Ser Ser Gly Gln Val Met
            515                 520                 525

Asn Phe Lys Gly Asp Ile Ile Val Val Tyr Val Ser Gln Thr Ser Gln
530                 535                 540

Glu Gly Pro Gly Ser Ala Glu Pro Glu Ser Pro Val Gly Arg Pro
545                 550                 555                 560

Val Gln Glu Glu Thr Leu Ala His Arg Asp Ser Phe Ala Gly Thr Ala
                565                 570                 575

Pro Arg Phe Pro Asp Val Cys Ala Thr Gly Ala Gly Leu Gln Glu Gln
                580                 585                 590

Gly Ala Pro Arg Gln Lys Asp Gly Thr Ser Arg Pro Val Gln Glu Gln
            595                 600                 605

Gly Gly Ala Gln Thr Ser Leu His Thr Gln Gly Ser Gly Gln Cys Ala
            610                 615                 620

Glu
625

(2) INFORMATION FOR SEQ ID NO:16:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:16:

Met Glu Thr Asp Thr Leu Leu Leu Trp Val Leu Leu Leu Trp Val Pro
  1                 5                  10                  15

Gly Ser Thr Gly
            20

(2) INFORMATION FOR SEQ ID NO:17:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:17:

Asp Tyr Lys Asp Glu
```

```
                               5

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:18:

His His His His His His
                      5

(2) INFORMATION FOR SEQ ID NO:19:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:19:

Arg Met Lys Gln Ile Glu Asp Lys Ile Glu Glu Ile Leu Ser Lys Ile
 1               5                  10                  15

Tyr His Ile Glu Asn Glu Ile Ala Arg Ile Lys Lys Leu Ile Gly Glu
            20                  25                  30

Arg
```

RECEPTOR ACTIVATOR OF NF-κB

CROSS-REFERENCE TO RELATED PATENT APPLICATIONS

This application is a continuation of U.S. provisional application No. 60/064,671, filed Oct. 14, 1997, and a continuation of U.S. provisional application No. 60/077,181, filed Mar. 7, 1997, and a continuation of U.S. provisional application No. 60/059,978, filed Dec. 23, 1996.

TECHNICAL FIELD OF THE INVENTION

The present invention relates generally to the field of cytokine receptors, and more specifically to cytokine receptor/ligand pairs having immunoregulatory activity.

BACKGROUND OF THE INVENTION

Efficient functioning of the immune system requires a fine balance between cell proliferation and differentiation and cell death, to ensure that the immune system is capable of reacting to foreign, but not self antigens. Integral to the process of regulating the immune and inflammatory response are various members of the Tumor Necrosis Factor (TNF) Receptor/Nerve Growth Factor Receptor superfamily (Smith et al., Science 248: 1019; 1990). This family of receptors includes two different TNF receptors (Type I and Type II; Smith et al., supra; and Schall et al., Cell 61: 361, 1990), nerve growth factor receptor (Johnson et al., Cell 47: 545, 1986), B cell antigen CD40 (Stamenkovic et al., EMBO J. 8: 1403, 1989), CD27 (Camerini et al., J. Immunol. 147: 3165, 1991), CD30 (Durkop et al., Cell 68: 421, 1992), T cell antigen OX40 (Mallett et al., EMBO J. 9: 1063, 1990), human Fas antigen (Itoh et al., Cell 66: 233, 1991), murine 4-1BB receptor (Kwon et al., Proc. Natl. Acad. Sci. USA 86: 1963, 1989) and a receptor referred to as Apoptosis-Inducing Receptor (AIR; U.S. Ser. No. 08/720,864, filed Oct. 4, 1996).

CD40 is a receptor present on B lymphocytes, epithelial cells and some carcinoma cell lines that interacts with a ligand found on activated T cells, CD40L (U.S. Ser. No. 08/249,189, filed May 24, 1994). The interaction of this ligand/receptor pair is essential for both the cellular and humoral immune response. Signal transduction via CD40 is mediated through the association of the cytoplasmic domain of this molecule with members of the TNF receptor-associated factors (TRAFs; Baker and Reddy, Oncogene 12: 1, 1996). It has recently been found that mice that are defective in TRAF3 expression due to a targeted disruption in the gene encoding TRAF3 appear normal at birth but develop progressive hypoglycemia and depletion of peripheral white cells, and die by about ten days of age (Xu et al., Immunity 5: 407, 1996). The immune responses of chimeric mice reconstituted with TRAF3$^{-/-}$ fetal liver cells resemble those of CD40-deficient mice, although TRAF3$^{-/-}$ B cells appear to be functionally normal.

The critical role of TRAF3 in signal transduction may be in its interaction with one of the other members of the TNF receptor superfamily, for example, CD30 or CD27, which are present on T cells. Alternatively, there may be other, as yet unidentified members of this family of receptors that interact with TRAF3 and play an important role in postnatal development as well as in the development of a competent immune system. Identifying additional members of the TNF receptor superfamily would provide an additional means of regulating the immune and inflammatory response, as well as potentially providing further insight into post-natal development in mammals.

SUMMARY OF THE INVENTION

The present invention provides a novel receptor, referred to as RANK (for receptor activator of NF-κB), that is a member of the TNF receptor superfamily. RANK is a Type I transmembrane protein having 616 amino acid residues that interacts with TRAF3. Triggering of RANK by over-expression, co-expression of RANK and membrane bound RANK ligand (RANKL), and with addition of soluble RANKL or agonistic antibodies to RANK results in the upregulation of the transcription factor NF-κB, a ubiquitous transcription factor that is most extensively utilized in cells of the immune system.

Soluble forms of the receptor can be prepared and used to interfere with signal transduction through membrane-bound RANK, and hence upregulation of NF-κB; accordingly, pharmaceutical compositions comprising soluble forms of the novel receptor are also provided. Inhibition of NF-κB by RANK antagonists may be useful in ameliorating negative effects of an inflammatory response that result from triggering of RANK, for example in treating toxic shock or sepsis, graft-versus-host reactions, or acute inflammatory reactions. Soluble forms of the receptor will also be useful in vitro to screen for agonists or antagonists of RANK activity.

The cytoplasmic domain of RANK will be useful in developing assays for inhibitors of signal transduction, for example, for screening for molecules that inhibit interaction of RANK with TRAF2 or TRAF3. Deleted forms and fusion proteins comprising the novel receptor are also disclosed.

The present invention also identifies a counterstructure, or ligand, for RANK, referred to as RANKL. RANKL is a Type 2 transmembrane protein with an intracellular domain of less than about 50 amino acids, a transmembrane domain and an extracellular domain of from about 240 to 250 amino acids. Similar to other members of the TNF family to which it belongs, RANKL has a 'spacer' region between the transmembrane domain and the receptor binding domain that is not necessary for receptor binding. Accordingly, soluble forms of RANKL can comprise the entire extracellular domain or fragments thereof that include the receptor binding region.

These and other aspects of the present invention will become evident upon reference to the following detailed description of the invention.

DETAILED DESCRIPTION OF THE INVENTION

Figure 1:
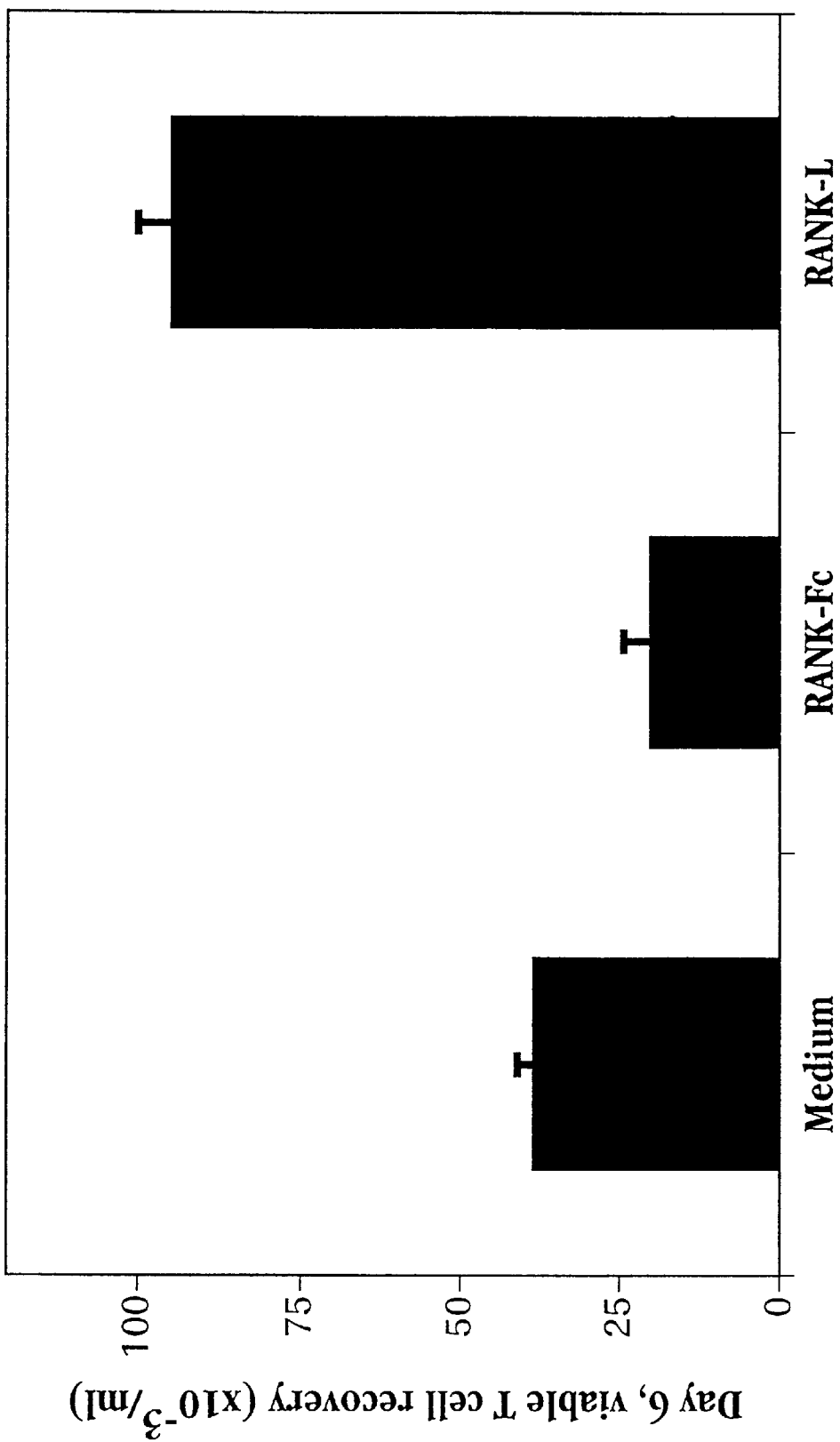
FIG. 1 demonstrates the influence of RANK.Fc and hRANKL on activated T cell growth. Human peripheral blood T cells were cultured as described in Example 12; viable T cell recovery was determined by triplicate trypan blue countings.

A novel partial cDNA insert with a predicted open reading frame having some similarity to CD40 was identified in a database containing sequence information from cDNAs generated from human bone marrow-derived dendritic cells (DC). The insert was used to hybridize to colony blots generated from a DC cDNA library containing full-length cDNAs. Several colony hybridizations were performed, and two clones (SEQ ID NOs:1 and 3) were isolated. SEQ ID NO:5 shows the nucleotide and amino acid sequence of a predicted full-length protein based on alignment of the overlapping sequences of SEQ ID NOs:1 and 3.

RANK is a member of the TNF receptor superfamily; it most closely resembles CD40 in the extracellular region. Similar to CD40, RANK associates with TRAF2 and TRAF3 (as determined by co-immunoprecipitation assays substantially as described by Rothe et al., Cell 83: 1243, 1995). TRAFs are critically important in the regulation of the immune and inflammatory response. Through their association with various members of the TNF receptor superfamily, a signal is transduced to a cell. That signal results in the proliferation, differentiation or apoptosis of the cell, depending on which receptor(s) is/are triggered and which TRAF(s) associate with the receptor(s); different signals can be transduced to a cell via coordination of various signaling events. Thus, a signal transduced through one member of this family may be proliferative, differentiative or apoptotic, depending on other signals being transduced to the cell, and/or the state of differentiation of the cell. Such exquisite regulation of this proliferative/apoptotic pathway is necessary to develop and maintain protection against pathogens; imbalances can result in autoimmune disease.

RANK is expressed on epithelial cells, some B cell lines, and on activated T cells. However, its expression on activated T cells is late, about four days after activation. This time course of expression coincides with the expression of Fas, a known agent of apoptosis. RANK may act as an anti-apoptotic signal, rescuing cells that express RANK from apoptosis as CD40 is known to do. Alternatively, RANK may confirm an apoptotic signal under the appropriate circumstances, again similar to CD40. RANK and its ligand are likely to play an integral role in regulation of the immune and inflammatory response.

Moreover, the post-natal lethality of mice having a targeted disruption of the TRAF3 gene demonstrates the importance of this molecule not only in the immune response but in development. The isolation of RANK, as a protein that associates with TRAF3, and its ligand will allow further definition of this signaling pathway, and development of diagnostic and therapeutic modalities for use in the area of autoimmune and/or inflammatory disease.

DNAs, Proteins and Analogs

The present invention provides isolated RANK polypeptides and analogs (or muteins) thereof having an activity exhibited by the native molecule (i.e, RANK muteins that bind specifically to a RANK ligand expressed on cells or immobilized on a surface or to RANK-specific antibodies; soluble forms thereof that inhibit RANK ligand-induced signaling through RANK). Such proteins are substantially free of contaminating endogenous materials and, optionally, without associated native-pattern glycosylation. Derivatives of RANK within the scope of the invention also include various structural forms of the primary proteins which retain biological activity. Due to the presence of ionizable amino and carboxyl groups, for example, a RANK protein may be in the form of acidic or basic salts, or may be in neutral form. Individual amino acid residues may also be modified by oxidation or reduction. The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Derivatives of RANK may also be obtained by the action of cross-linking agents, such as M-maleimidobenzoyl succinimide ester and N-hydroxysuccinimide, at cysteine and lysine residues. The inventive proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, the proteins may be used to selectively bind (for purposes of assay or purification) antibodies raised against the proteins or against other proteins which are similar to RANK or RANKL, as well as other proteins that bind RANK or RANKL or homologs thereof.

Soluble forms of RANK are also within the scope of the invention. The nucleotide and predicted amino acid sequence of the RANK is shown in SEQ ID NOs:1 through 6. Computer analysis indicated that the protein has an N-terminal signal peptide; the predicted cleavage site follows residue 24. Those skilled in the art will recognize that the actual cleavage site may be different than that predicted by computer analysis. Thus, the N-terminal amino acid of the cleaved peptide is expected to be within about five amino acids on either side of the predicted, preferred cleavage site following residue 24. Moreover a soluble form beginning with amino acid 33 was prepared; this soluble form bound RANKL. The signal peptide is predicted to be followed by a 188 amino acid extracellular domain, a 21 amino acid transmembrane domain, and a 383 amino acid cytoplasmic tail.

Soluble RANK comprises the signal peptide and the extracellular domain (residues 1 to 213 of SEQ ID NO:6) or a fragment thereof. Alternatively, a different signal peptide can be substituted for the native leader, beginning with residue 1 and continuing through a residue selected from the group consisting of amino acids 24 through 33 (inclusive) of SEQ ID NO:6. Moreover, fragments of the extracellular domain will also provide soluble forms of RANK. Fragments can be prepared using known techniques to isolate a desired portion of the extracellular region, and can be prepared, for example, by comparing the extracellular region with those of other members of the TNFR family and selecting forms similar to those prepared for other family members. Alternatively, unique restriction sites or PCR techniques that are known in the art can be used to prepare numerous truncated forms which can be expressed and analyzed for activity.

Fragments can be prepared using known techniques to isolate a desired portion of the extracellular region, and can be prepared, for example, by comparing the extracellular region with those of other members of the TNFR family (of which RANK is a member) and selecting forms similar to those prepared for other family members. Alternatively, unique restriction sites or PCR techniques that are known in the art can be used to prepare numerous truncated forms which can be expressed and analyzed for activity.

Other derivatives of the RANK proteins within the scope of this invention include covalent or aggregative conjugates of the proteins or their fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of RANK proteins and homologs (e.g., poly-His). The amino acid sequence of the inventive proteins can also be linked to an identification peptide such as that described by Hopp et al., *Bio/Technology* 6: 1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli*.

Fusion proteins further comprise the amino acid sequence of a RANK linked to an immunoglobulin Fc region. An exemplary Fc region is a human $IgG_1$ having a nucleotide an amino acid sequence set forth in SEQ ID NO:8. Fragments of an Fc region may also be used, as can Fc muteins. For example, certain residues within the hinge region of an Fc region are critical for high affinity binding to FcγRI. Canfield and Morrison (*J. Exp. Med.* 173: 1483; 1991) reported that $Leu_{(234)}$ and $Leu_{(235)}$ were critical to high affinity binding of $IgG_3$ to FcγRI present on U937 cells. Similar results were obtained by Lund et al. (*J. Immunol.* 147: 2657, 1991; *Molecular Immunol.* 29: 53, 1991). Such mutations, alone or in combination, can be made in an $IgG_1$ Fc region to decrease the affinity of $IgG_1$ for FcR.

Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four RANK regions.

In another embodiment, RANK proteins further comprise an oligomerizing peptide such as a leucine zipper domain. Leucine zippers were originally identified in several DNA-binding proteins (Landschulz et al., *Science* 240: 1759, 1988). Leucine zipper domain is a term used to refer to a conserved peptide domain present in these (and other) proteins, which is responsible for dimerization of the proteins. The leucine zipper domain (also referred to herein as an oligomerizing, or oligomer-forming, domain) comprises a repetitive heptad repeat, with four or five leucine residues interspersed with other amino acids. Examples of leucine zipper domains are those found in the yeast transcription factor GCN4 and a heat-stable DNA-binding protein found in rat liver (C/EBP; Landschulz et al., *Science* 243: 1681, 1989). Two nuclear transforming proteins, fos and jun, also exhibit leucine zipper domains, as does the gene product of the murine proto-oncogene, c-myc (Landschulz et al., *Science* 240: 1759, 1988). The products of the nuclear oncogenes fos and jun comprise leucine zipper domains preferentially form a heterodimer (O'Shea et al., *Science* 245: 646, 1989; Turner and Tjian, *Science* 243: 1689, 1989). The leucine zipper domain is necessary for biological activity (DNA binding) in these proteins.

The fusogenic proteins of several different viruses, including paramyxovirus, coronavirus, measles virus and many retroviruses, also possess leucine zipper domains (Buckland and Wild, *Nature* 338: 547,1989; Britton, *Nature* 353: 394, 1991; Delwart and Mosialos, *AIDS Research and Human Retroviruses* 6: 703, 1990). The leucine zipper domains in these fusogenic viral proteins are near the transmembrane region of the proteins; it has been suggested that the leucine zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88: 3523, 1991).

Leucine zipper domains have also been recently reported to play a role in oligomerization of heat-shock transcription factors (Rabindran et al., *Science* 259: 230, 1993).

Leucine zipper domains fold as short, parallel coiled coils. (O'Shea et al., *Science* 254: 539; 1991) The general architecture of the parallel coiled coil has been well characterized, with a "knobs-into-holes" packing as proposed by Crick in 1953 (*Acta Crystallogr.* 6: 689). The dimer formed by a leucine zipper domain is stabilized by the heptad repeat, designated $(abcdefg)_n$ according to the notation of McLachlan and Stewart (*J. Mol. Biol.* 98: 293; 1975), in which residues a and d are generally hydrophobic residues, with d being a leucine, which line up on the same face of a helix. Oppositely-charged residues commonly occur at positions g and e. Thus, in a parallel coiled coil formed from two helical leucine zipper domains, the "knobs" formed by the hydrophobic side chains of the first helix are packed into the "holes" formed between the side chains of the second helix.

The leucine residues at position d contribute large hydrophobic stabilization energies, and are important for dimer formation (Krystek et al., *Int. J. Peptide Res.* 38: 229, 1991). Lovejoy et al. recently reported the synthesis of a triple-stranded α-helical bundle in which the helices run up-up-down (*Science* 259: 1288, 1993). Their studies confirmed that hydrophobic stabilization energy provides the main driving force for the formation of coiled coils from helical monomers. These studies also indicate that electrostatic interactions contribute to the stoichiometry and geometry of coiled coils.

Several studies have indicated that conservative amino acids may be substituted for individual leucine residues with minimal decrease in the ability to dimerize; multiple changes, however, usually result in loss of this ability (Landschulz et al., *Science* 243: 1681, 1989; Turner and Tjian, *Science* 243: 1689, 1989; Hu et al., *Science* 250: 1400, 1990). van Heekeren et al. reported that a number of different amino residues can be substituted for the leucine residues in the leucine zipper domain of GCN4, and further found that some GCN4 proteins containing two leucine substitutions were weakly active (*Nucl. Acids Res.* 20: 3721, 1992). Mutation of the first and second heptadic leucines of the leucine zipper domain of the measles virus fusion protein (MVF) did not affect syncytium formation (a measure of virally-induced cell fusion); however, mutation of all four leucine residues prevented fusion completely (Buckland et al., *J. Gen. Virol.* 73: 1703, 1992). None of the mutations affected the ability of MVF to form a tetramer.

Amino acid substitutions in the a and d residues of a synthetic peptide representing the GCN4 leucine zipper domain have been found to change the oligomerization properties of the leucine zipper domain (Alber, Sixth Symposium of the Protein Society, San Diego, Calif.). When all residues at position a are changed to isoleucine, the leucine zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes. Peptides containing these substitutions are still referred to as leucine zipper domains.

Also included within the scope of the invention are fragments or derivatives of the intracellular domain of RANK. Such fragments are prepared by any of the hereinmentioned techniques, and include peptides that are identical to the cytoplasmic domain of RANK as shown in SEQ ID NO:5, or of murine RANK as shown in SEQ ID NO: 15, and those that comprise a portion of the cytoplasmic region. All techniques used in preparing soluble forms may also be used in preparing fragments or analogs of the cytoplasmic domain (i.e., RT-PCR techniques or use of selected restriction enzymes to prepare truncations). DNAs encoding all or a fragment of the intracytoplasmic domain will be useful in identifying other proteins that are associated with RANK signalling, for example using the immunoprecipitation techniques described herein, or another technique such as a yeast two-hybrid system (Rothe et al., supra).

The present invention also includes RANK with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of DNAs encoding the inventive proteins in bacteria such as $E.\ coli$ provides non-glycosylated molecules. Functional mutant analogs of RANK protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between Al and Z, or an amino acid other than Asn between Asn and $A_1$.

RANK protein derivatives may also be obtained by mutations of the native RANK or subunits thereof. A RANK mutated protein, as referred to herein, is a polypeptide homologous to a native RANK protein, respectively, but which has an amino acid sequence different from the native protein because of one or a plurality of deletions, insertions or substitutions. The effect of any mutation made in a DNA encoding a mutated peptide may be easily determined by analyzing the ability of the mutated peptide to bind its counterstructure in a specific manner. Moreover, activity of RANK analogs, muteins or derivatives can be determined by any of the assays described herein (for example, inhibition of the ability of RANK to activate transcription).

Analogs of the inventive proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

When a deletion or insertion strategy is adopted, the potential effect of the deletion or insertion on biological activity should be considered. Subunits of the inventive proteins may be constructed by deleting terminal or internal residues or sequences. Soluble forms of RANK can be readily prepared and tested for their ability to inhibit RANK-induced NF-κB activation. Polypeptides corresponding to the cytoplasmic regions, and fragments thereof (for example, a death domain) can be prepared by similar techniques. Additional guidance as to the types of mutations that can be made is provided by a comparison of the sequence of RANK to proteins that have similar structures, as well as by performing structural analysis of the inventive RANK proteins.

Generally, substitutions should be made conservatively; i.e., the most preferred substitute amino acids are those which do not affect the biological activity of RANK (i.e., ability of the inventive proteins to bind antibodies to the corresponding native protein in substantially equivalent a manner, the ability to bind the counterstructure in substantially the same manner as the native protein, the ability to transduce a RANK signal, or ability to induce NF-κB activation upon overexpression in transient transfection systems, for example). Examples of conservative substitutions include substitution of amino acids outside of the binding domain(s) (either ligand/receptor or antibody binding areas for the extracellular domain, or regions that interact with other, intracellular proteins for the cytoplasmic domain), and substitution of amino acids that do not alter the secondary and/or tertiary structure of the native protein. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Mutations in nucleotide sequences constructed for expression of analog proteins or fragments thereof must, of course, preserve the reading frame phase of the coding sequences and preferably will not create complementary regions that could hybridize to produce secondary mRNA structures such as loops or hairpins which would adversely affect translation of the mRNA.

Not all mutations in the nucleotide sequence which encodes a RANK protein or fragments thereof will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known $E.\ coli$ preference codons for $E.\ coli$ expression.

Although a mutation site may be predetermined, it is not necessary that the nature of the mutation per se be predetermined. For example, in order to select for optimum characteristics of mutants, random mutagenesis may be conducted and the expressed mutated proteins screened for the desired activity. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42: 133, 1986); Bauer et al. (*Gene* 37: 73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Other embodiments of the inventive proteins include RANK polypeptides encoded by DNAs capable of hybridizing to the DNA of SEQ ID NO:6 under moderately stringent conditions (prewashing solution of 5× SSC, 0.5% SDS, 1.0 mM EDTA (pH 8.0) and hybridization conditions of 50° C., 5×, overnight) to the DNA sequences encoding RANK, or more preferably under stringent conditions (for example, hybridization in 6× SSC at 63° C. overnight; washing in 3× at 55° C.), and other sequences which are degenerate to those which encode the RANK. In one embodiment, RANK polypeptides are at least about 70% identical in amino acid sequence to the amino acid sequence of native RANK protein as set forth in SEQ ID NO:5. In a preferred embodiment, RANK polypeptides are at least about 80% identical in amino acid sequence to the native form of RANK; most preferred polypeptides are those that are at least about 90% identical to native RANK.

Percent identity may be determined using a computer program, for example, the GAP computer program described by Devereux et al. (*Nucl. Acids Res.* 12: 387, 1984) and available from the University of Wisconsin Genetics Computer Group (UWGCG). For fragments derived from the RANK protein, the identity is calculated based on that portion of the RANK protein that is present in the fragment The biological activity of RANK analogs or muteins can be determined by testing the ability of the analogs or muteins to inhibit activation of transcription, for example as described in the Examples herein. Alternatively, suitable assays, for example, an enzyme immunoassay or a dot blot, employing an antibody that binds native RANK, or a soluble form of RANKL, can be used to assess the activity of RANK analogs or muteins, as can assays that employ cells expressing RANKL. Suitable assays also include, for example, signal transduction assays and methods that evaluate the ability of the cytoplasmic region of RANK to associate with other intracellular proteins (i.e., TRAFs 2 and 3) involved in signal transduction will also be useful to assess the activity of RANK analogs or muteins. Such methods are well known in the art.

Fragments of the RANK nucleotide sequences are also useful. In one embodiment, such fragments comprise at least about 17 consecutive nucleotides, preferably at least about 25 nucleotides, more preferably at least 30 consecutive nucleotides, of the RANK DNA disclosed herein. DNA and RNA complements of such fragments are provided herein, along with both single-stranded and double-stranded forms of the RANK DNA of SEQ ID NO:5, and those encoding the aforementioned polypeptides. A fragment of RANK DNA generally comprises at least about 17 nucleotides, preferably from about 17 to about 30 nucleotides. Such nucleic acid fragments (for example, a probe corresponding to the extracellular domain of RANK) are used as a probe or as primers in a polymerase chain reaction (PCR).

The probes also find use in detecting the presence of RANK nucleic acids in in vitro assays and in such procedures as Northern and Southern blots. Cell types expressing RANK can be identified as well. Such procedures are well known, and the skilled artisan can choose a probe of suitable length, depending on the particular intended application. For PCR, 5' and 3' primers corresponding to the termini of a desired RANK DNA sequence are employed to amplify that sequence, using conventional techniques.

Other useful fragments of the RANK nucleic acids are antisense or sense oligonucleotides comprising a single-stranded nucleic acid sequence (either RNA or DNA) capable of binding to target RANK mRNA (sense) or RANK DNA (antisense) sequences. The ability to create an antisense or a sense oligonucleotide, based upon a cDNA sequence for a given protein is described in, for example, Stein and Cohen, *Cancer Res.* 48: 2659, 1988 and van der Krol et al., *BioTechniques* 6: 958, 1988.

Uses of DNAs, Proteins and Analogs

The RANK DNAs, proteins and analogs described herein will have numerous uses, including the preparation of pharmaceutical compositions. For example, soluble forms of RANK will be useful as antagonists of RANK-mediated NF-κB activation, as well as to inhibit transduction of a signal via RANK. RANK compositions (both protein and DNAs) will also be useful in development of both agonistic and antagonistic antibodies to RANK. The inventive DNAs are useful for the expression of recombinant proteins, and as probes for analysis (either quantitative or qualitative) of the presence or distribution of RANK transcripts.

The inventive proteins will also be useful in preparing kits that are used to detect soluble RANK or RANKL, or monitor RANK-related activity, for example, in patient specimens. RANK proteins will also find uses in monitoring RANK-related activity in other samples or compositions, as is necessary when screening for antagonists or mimetics of this activity (for example, peptides or small molecules that inhibit or mimic, respectively, the interaction). A variety of assay formats are useful in such kits, including (but not limited to) ELISA, dot blot, solid phase binding assays (such as those using a biosensor), rapid format assays and bioassays.

The purified RANK according to the invention will facilitate the discovery of inhibitors of RANK, and thus, inhibitors of an inflammatory response (via inhibition of NF-κB activation). The use of a purified RANK polypeptide in the screening for potential inhibitors is important and can virtually eliminate the possibility of interfering reactions with contaminants. Such a screening assay can utilize either the extracellular domain of RANK, the intracellular domain, or a fragment of either of these polypeptides. Detecting the inhibiting activity of a molecule would typically involve use of a soluble form of RANK derived from the extracellular domain in a screening assay to detect molecules capable of binding RANK and inhibiting binding of, for example, an agonistic antibody or RANKL, or using a polypeptide derived from the intracellular domain in an assay to detect inhibition of the interaction of RANK and other, intracellular proteins involved in signal transduction.

Moreover, in vitro systems can be used to ascertain the ability of molecules to antagonize or agonize RANK activity. Included in such methods are uses of RANK chimeras, for example, a chimera of the RANK intracellular domain and an extracellular domain derived from a protein having a known ligand. The effects on signal transduction of various molecule can then be monitored by utilizing the known ligand to transduce a signal.

In addition, RANK polypeptides can also be used for structure-based design of RANK-inhibitors. Such structure-based design is also known as "rational drug design." The RANK polypeptides can be three-dimensionally analyzed by, for example, X-ray crystallography, nuclear magnetic resonance or homology modeling, all of which are well-known methods. The use of RANK structural information in molecular modeling software systems to assist in inhibitor design is also encompassed by the invention. Such computer-assisted modeling and drug design may utilize information such as chemical conformational analysis, electrostatic potential of the molecules, protein folding, etc. A particular method of the invention comprises analyzing the three dimensional structure of RANK for likely binding sites of substrates, synthesizing a new molecule that incorporates a predictive reactive site, and assaying the new molecule as described above.

Expression of Recombinant RANK

The proteins of the present invention are preferably produced by recombinant DNA methods by inserting a DNA sequence encoding RANK protein or an analog thereof into a recombinant expression vector and expressing the DNA sequence in a recombinant expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding RANK, or homologs, muteins or bioequivalent analogs thereof, operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding RANK, or homologs or analogs thereof which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. E. coli is typically transformed using derivatives of pBR322, a plasmid derived from an E. coli species (Bolivar et al., Gene 2: 95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., Nature 275: 615, 1978; and Goeddel et al., Nature 281: 544, 1979), the tryptophan (trp) promoter system (Goeddel et al., Nucl. Acids Res. 8: 4057, 1980; and EPA 36,776) and tac promoter (Maniatis, Molecular Cloning: A Laboratory Manual, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in E. coli strain JMB9 (ATCC 37092) and pPLc28, resident in E. coli RR1 (ATCC 53082).

Suitable promoter sequences in yeast vectors include the promoters for metallothionein, 3-phosphoglycerate kinase (Hitzeman et al., J. Biol. Chem. 255: 2073, 1980) or other glycolytic enzymes (Hess et al., J. Adv. Enzyme Reg. 7: 149, 1968; and Holland et al., Biochem. 17: 4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in E. coli (Amp$^r$ gene and origin of replication) and yeast DNA sequences including a glucose-repressible ADH2 promoter and α-factor secretion leader. The ADH2 promoter has been described by Russell et al. (J. Biol. Chem. 258: 2674, 1982) and Beier et al. (Nature 300: 724, 1982). The yeast α-factor leader, which directs secretion of heterologous proteins, can be inserted between the promoter and the structural gene to be expressed. See, e.g., Kurjan et al., Cell 30: 933, 1982; and Bitter et al., Proc. Natl. Acad. Sci. USA 81: 5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., Nature 273: 113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (Mol. Cell. Biol. 3: 280, 1983).

A useful system for stable high level expression of mammalian receptor cDNAs in C127 murine mammary epithelial cells can be constructed substantially as described by Cosman et al. (Mol. Immunol. 23: 935, 1986). A preferred eukaryotic vector for expression of RANK DNA is referred to as pDC406 (McMahan et al., *EMBO J.* 10: 2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as DC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the proteins of the present invention. Transformed host cells may express the desired protein (RANK, or homologs or analogs thereof), but host cells transformed for purposes of cloning or amplifying the inventive DNA do not need to express the protein. Expressed proteins will preferably be secreted into the culture supernatant, depending on the DNA selected, but may be deposited in the cell membrane.

Suitable host cells for expression of proteins include prokaryotes, yeast or higher eukaryotic cells under the control of appropriate promoters. Prokaryotes include gram negative or gram positive organisms, for example *E. coli* or *Bacillus* spp. Higher eukaryotic cells include established cell lines of mammalian origin as described below. Cell-free translation systems could also be employed to produce proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, New York, 1985), the relevant disclosure of which is hereby incorporated by reference.

Prokaryotic expression hosts may be used for expression of RANK, or homologs or analogs thereof that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Recombinant RANK may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the $2\mu$ yeast plasmid or an autonomously replicating sequence (ARS), promoter, DNA encoding the protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75: 1929, 1978, selecting for Trp$^+$ transformants in a selective medium consisting of 0.67% yeast nitrogen base, 0.5% casamino acids, 2% glucose, 10 $\mu$g/ml adenine and 20 $\mu$g/ml uracil. Host strains transformed by vectors comprising the ADH2 promoter may be grown for expression in a rich medium consisting of 1% yeast extract, 2% peptone, and 1% glucose supplemented with 80 $\mu$g/ml adenine and 80 $\mu$g/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6: 47 (1988). Examples of suitable mammalian host cell lines include the COS-7 lines of monkey kidney cells, described by Gluzman (*Cell* 23: 175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of Recombinant RANK

Purified RANK, and homologs or analogs thereof are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying RANK and homologs thereof. For example, a RANK expressed as a fusion protein comprising an immunoglobulin Fc region can be purified using Protein A or Protein G affinity chromatography. Moreover, a RANK protein comprising an oligomerizing zipper domain may be purified on a resin comprising an antibody specific to the oligomerizing zipper domain. Monoclonal antibodies against the RANK protein may also be useful in affinity chromatography purification, by utilizing methods that are well-known in the art. A ligand may also be used to prepare an affinity matrix for affinity purification of RANK.

Finally, one or more reversed-phase high performance liquid chromatography (RP-HPLC) steps employing hydrophobic RP-HPLC media, e.g., silica gel having pendant methyl or other aliphatic groups, can be employed to further purify a RANK composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant protein can be disrupted by any convenient method, including freeze-thaw cycling, sonication, mechanical disruption, or use of cell lysing agents.

Fermentation of yeast which express the inventive protein as a secreted protein greatly simplifies purification. Secreted recombinant protein resulting from a large-scale fermentation can be purified by methods analogous to those disclosed by Urdal et al. (*J. Chromatog.* 296: 171, 1984). This reference describes two sequential, reversed-phase HPLC steps for purification of recombinant human GM-CSF on a preparative HPLC column.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Uses and Administration of RANK Compositions

The present invention provides methods of using therapeutic compositions comprising an effective amount of a protein and a suitable diluent and carrier, and methods for regulating an immune or inflammatory response. The use of RANK in conjunction with soluble cytokine receptors or cytokines, or other immunoregulatory molecules is also contemplated.

For therapeutic use, purified protein is administered to a patient, preferably a human, for treatment in a manner appropriate to the indication. Thus, for example, RANK protein compositions administered to regulate immune function can be given by bolus injection, continuous infusion, sustained release from implants, or other suitable technique. Typically, a therapeutic agent will be administered in the form of a composition comprising purified RANK, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Soluble forms of RANK and other RANK antagonists such as antagonistic monoclonal antibodies can be administered for the purpose of inhibiting RANK-induced induction of NF-κB activity. NF-κB is a transcription factor that is utilized extensively by cells of the immune system, and plays a role in the inflammatory response. Thus, inhibitors of RANK signalling will be useful in treating conditions in which signalling through RANK has given rise to negative consequences, for example, toxic or septic shock, or graft-versus-host reactions. They may also be useful in interfering with the role of NF-κB in cellular transformation. Tumor cells are more responsive to radiation when their NF-κB is blocked; thus, soluble RANK (or other antagonists of RANK signalling) will be useful as an adjunct therapy for disease characterized by neoplastic cells that express RANK.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

The example describes the identification and isolation of a DNA encoding a novel member of the TNF receptor superfamily. A partial cDNA insert with a predicted open reading frame having some similarity to CD40 (a cell-surface antigen present on the surface of both normal and neoplastic human B cells that has been shown to play an important role in B-cell proliferation and differentiation; Stamenkovic et al., *EMBO J.* 8: 1403, 1989), was identified in a database containing sequence information from cDNAs generated from human bone marrow-derived dendritic cells (DC). The insert was excised from the vector by restriction endonuclease digestion, gel purified, labeled with $^{32}$P, and used to hybridize to colony blots generated from a DC cDNA library containing larger cDNA inserts using high stringency hybridization and washing techniques (hybridization in 5× SSC, 50% formamide at 42° C. overnight, washing in 0.5× SSC at 63° C.); other suitable high stringency conditions are disclosed in Sambrook et al. in *Molecular Cloning: A Laboratory Manual,* 2nd ed. (Cold Spring Harbor Laboratory, Cold Spring Harbor, N.Y.; 1989), 9.52–9.55. Initial experiments yielded a clone referred to as 9D–8A (SEQ ID NO:1); subsequent analysis indicated that this clone contained all but the extreme 5' end of a novel cDNA, with predicted intron sequence at the extreme 5' end (nucleotides 1–92 of SEQ ID NO:1). Additional colony hybridizations were performed, and a second clone was isolated. The second clone, referred to as 9D–15C (SEQ ID NO:3), contained the 5' end without intron interruption but not the full 3' end. SEQ ID NO:5 shows the nucleotide and amino acid sequence of a predicted full-length protein based on alignment of the overlapping sequences of SEQ ID NOs:1 and 3.

The encoded protein was designated RANK, for receptor activator of NF-κB. The cDNA encodes a predicted Type 1 transmembrane protein having 616 amino acid residues, with a predicted 24 amino acid signal sequence (the computer predicted cleavage site is after Leu24), a 188 amino acid extracellular domain, a 21 amino acid transmembrane domain, and a 383 amino acid cytoplasmic tail. The extracellular region of RANK displayed significant amino acid homology (38.5% identity, 52.3% similarity) to CD40. A cloning vector (pBluescriptSK⁻) containing human RANK sequence, designated pBluescript:huRANK (in *E. coli* DH10B), was deposited with the American Type Culture Collection, Rockville, Md. (ATCC) on Dec. 20, 1996, under terms of the Budapest Treaty, and given accession number 98285.

EXAMPLE 2

This example describes construction of a RANK DNA construct to express a RANK/Fc fusion protein. A soluble form of RANK fused to the Fc region of human $IgG_1$ was constructed in the mammalian expression vector pDC409 (U.S. Ser. No. 08/571,579). This expression vector encodes the leader sequence of the Cytomegalovirus (CMV) open reading frame R27080 (SEQ ID NO:9), followed by amino acids 33–213 of RANK, followed by a mutated form of the constant domain of human $IgG_1$ that exhibits reduced affinity for Fc receptors (SEQ ID NO:8; for the fusion protein, the Fc portion of the construct consisted of Arg3 through Lys232). An alternative expression vector encompassing amino acids 1–213 of RANK (using the native leader sequence) followed by the $IgG_1$ mutein was also prepared. Both expression vectors were found to induce high levels of expression of the RANK/Fc fusion protein in transfected cells.

To obtain RANK/Fc protein, a RANK/Fc expression plasmid is transfected into CV-1/EBNA cells, and supernatants are collected for about one week. The RANK/Fc fusion protein is purified by means well-known in the art for purification of Fc fusion proteins, for example, by protein A sepharose column chromatography according to manufacturer's recommendations (i.e., Pharmacia, Uppsala, Sweden). SDS-polyacrylamide gel electrophoresis analysis indicted that the purified RANK/Fc protein migrated with a molecular weight of ~55 kDa in the presence of a reducing agent, and at a molecular weight of ~110 kDa in the absence of a reducing agent.

N-terminal amino acid sequencing of the purified protein made using the CMV R27080 leader showed 60% cleavage after Ala20, 20% cleavage after Pro22 and 20% cleavage after Arg28 (which is the Furin cleavage site; amino acid residues are relative to SEQ ID NO:9); N-terminal amino acid analysis of the fusion protein expressed with the native leader showed cleavage predominantly after Gln25 (80% after Gln25 and 20% after Arg23; amino acid residues are relative to SEQ ID NO:6, full-length RANK). Both fusion proteins were able to bind a ligand for RANK is a specific manner (i.e., they bound to the surface of various cell lines such as a murine thymoma cell line, EL4), indicating that the presence of additional amino acids at the N-terminus of RANK does not interfere with its ability to bind RANKL. Moreover, the construct comprising the CMV leader encoded RANK beginning at amino acid 33; thus, a RANK peptide having an N-terminus at an amino acid between Arg23 and Pro33, inclusive, is expected to be able to bind a ligand for RANK in a specific manner.

Other members of the TNF receptor superfamily have a region of amino acids between the transmembrane domain and the ligand binding domain that is referred to as a 'spacer' region, which is not necessary for ligand binding. In RANK, the amino acids between 196 and 213 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 213 and 196 of SEQ ID NO:6, although other amino acids in the spacer region may be utilized as a C-terminus.

EXAMPLE 3

This example illustrates the preparation of monoclonal antibodies against RANK. Preparations of purified recombinant RANK, for example, or transfected cells expressing high levels of RANK, are employed to generate monoclonal antibodies against RANK using conventional techniques, such as those disclosed in U.S. Pat. No. 4,411,993. DNA encoding RANK can also be used as an immunogen, for example, as reviewed by Pardoll and Beckerleg in *Immunity* 3: 165, 1995. Such antibodies are likely to be useful in interfering with RANK-induced signaling (antagonistic or blocking antibodies) or in inducing a signal by cross-linking RANK (agonistic antibodies), as components of diagnostic or research assays for RANK or RANK activity, or in affinity purification of RANK.

To immunize rodents, RANK immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. DNA may be given intradermally (Raz et al., *Proc. Natl. Acad. Sci. USA* 91: 9519, 1994) or intamuscularly (Wang et al., *Proc. Natl. Acad. Sci. USA* 90: 4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with RANK, for example, by adaptations of the techniques disclosed by Engvall et al., *Immunochem.* 8: 871 (1971) and in U.S. Pat. No. 4,703,004. A preferred screening technique is the antibody capture technique described by Beckman et al., *J. Immunol.* 144: 4212 (1990). Positive clones are then injected into the peritoneal cavities of syngeneic rodents to produce ascites containing high concentrations (>1 mg/ml) of anti-RANK monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to RANK protein.

Monoclonal antibodies were generated using RANK/Fc fusion protein as the immunogen. These reagents were screened to confirm reactivity against the RANK protein. Using the methods described herein to monitor the activity of the mAbs, both blocking (i.e., antibodies that bind RANK and inhibit binding of a ligand to RANK) and non-blocking (i.e., antibodies that bind RANK and do not inhibit ligand binding) were isolated.

EXAMPLE 4

This example illustrates the induction of NF-κB activity by RANK in 293/EBNA cells (cell line was derived by transfection of the 293 cell line with a gene encoding Epstein-Barr virus nuclear antigen-1 (EBNA-1) that constitutively express EBNA-1 driven from human CMV immediate-early enhancer/promoter). Activation of NF-κB activity was measured in 293/EBNA cells essentially as described by Yao et al. (*Immunity* 3: 811, 1995). Nuclear extracts were prepared and analyzed for NF-κB activity by a gel retardation assay using a 25 base pair oligonucleotide spanning the NF-κB binding sites. Two million cells were seeded into 10 cm dishes two days prior to DNA transfection and cultured in DMEM-F12 media containing 2.5% FBS (fetal bovine serum). DNA transfections were performed as described herein for the IL-8 promoter/reporter assays.

Nuclear extracts were prepared by solubilization of isolated nuclei with 400 mM NaCl (Yao et al., supra). Oligonucleotides containing an NF-κB binding site were annealed and endlabeled with $^{32}$P using T4 DNA polynucleotide kinase. Mobility shift reactions contained 10 μg of nuclear extract, 4 μg of poly(dI-dC) and 15,000 cpm labeled double-stranded oligonucleotide and incubated at room temperature for 20 minutes. Resulting protein-DNA complexes were resolved on a 6% native polyacrylamide gel in 0.25× Tris-borate-EDTA buffer.

Overexpression of RANK resulted in induction of NF-κB activity as shown by an appropriate shift in the mobility of the radioactive probe on the gel. Similar results were observed when RANK was triggered by a ligand that binds RANK and transduces a signal to cells expressing the receptor (i.e., by co-transfecting cells with human RANK and murine RANKL DNA; see Example 7 below), and would be expected to occur when triggering is done with agonistic antibodies.

EXAMPLE 5

This example describes a gene promoter/reporter system based on the human Interleukin-8 (IL-8) promoter used to analyze the activation of gene transcription in vivo. The induction of human IL-8 gene transcription by the cytokines Interleukin-1 (IL-1) or tumor necrosis factor-alpha (TNF-α) is known to be dependent upon intact NF-κB and NF-IL-6 transcription factor binding sites. Fusion of the cytokine-responsive IL-8 promoter with a cDNA encoding the murine IL-4 receptor (mIL-4R) allows measurement of promoter activation by detection of the heterologous reporter protein (mIL-4R) on the cell surface of transfected cells.

Human kidney epithelial cells (293/EBNA) are transfected (via the DEAE/DEXTRAN method) with plasmids encoding: 1). the reporter/promoter construct (referred to as pIL-8rep), and 2). the cDNA(s) of interest. DNA concentrations are always kept constant by the addition of empty vector DNA. The 293/EBNA cells are plated at a density of 2.5×10$^4$ cells/ml (3 ml/ well) in a 6 well plate and incubated for two days prior to transfection. Two days after transfection, the mIL-4 receptor is detected by a radioimmunoassay (RIA) described below.

In one such experiment, the 293/EBNA cells were co-transfected with DNA encoding RANK and with DNA encoding RANKL (see Example 7 below). Co-expression of this receptor and its counterstructure by cells results in activation of the signaling process of RANK. For such co-transfection studies, the DNA concentration/well for the DEAE transfection were as follows: 40 ng of pIL-8rep [pBluescriptSK$^-$ vector (Stratagene)]; 0.4 ng CD40 (DNA encoding CD40, a control receptor; pCDM8 vector); 0.4 ng RANK (DNA encoding RANK; pDC409 vector), and either 1–50 ng CD40L (DNA encoding the ligand for CD40, which acts as a positive control when co-transfected with CD40 and as a negative control when co-transfected with RANK; in pDC304) or RANKL (DNA encoding a ligand for RANK; in pDC406). Similar experiments can be done using soluble RANKL or agonistic antibodies to RANK to trigger cells transfected with RANK.

For the mIL-4R-specific RIA, a monoclonal antibody reactive with mIL-4R is labeled with $^{125}$I via a Chloramine T conjugation method; the resulting specific activity is typically 1.5×10$^{16}$ cpm/nmol. After 48 hours, transfected cells are washed once with media (DMEM(F12 5% FBS). Non-specific binding sites are blocked by the addition of pre-warmed binding media containing 5% non-fat dry milk and incubation at 37° C./5% $CO_2$ in a tissue culture incubator for one hour. The blocking media is decanted and binding buffer containing $^{125}$I anti-mIL-4R (clone M1; rat IgG1) is added to the cells and incubated with rocking at room temperature for 1 hour. After incubation of the cells with the radio-labeled antibody, cells are washed extensively with binding buffer (2×) and twice with phosphate-buffered saline (PBS). Cells are lysed in 1 ml of 0.5M NaOH, and total radioactivity is measured with a gamma counter.

Using this assay, 293/EBNA co-transfected with DNAs encoding RANK demonstrated transcriptional activation, as shown by detection of muIL-4R on the cell surface. Overexpression of RANK resulted in transcription of muIL-4R, as did triggering of the RANK by RANKL. Similar results are observed when RANK is triggered by agonistic antibodies.

EXAMPLE 6

This example illustrates the association of RANK with TRAF proteins. Interaction of RANK with cytoplasmic TRAF proteins was demonstrated by co-immunoprecipitation assays essentially as described by Hsu et al. (*Cell* 84: 299; 1996). Briefly, 293/EBNA cells were co-transfected with plasmids that direct the synthesis of RANK and epitope-tagged (FLAG®; SEQ ID NO:7) TRAF2 or TRAF3. Two days after transfection, surface proteins were labeled with biotin-ester, and cells were lysed in a buffer containing 0.5% NP-40. RANK and proteins associated with this receptor were immunoprecipitated with anti-RANK, washed extensively, resolved by electrophoretic separation on a 6–10% SDS polyacrylamide gel and electrophoretically transferred to a nitrocellulose membrane for Western blotting. The association of TRAF2 and TRAF3 proteins with RANK was visualized by probing the membrane with an antibody that specifically recognizes the FLAG® epitope. TRAFs 2 and 3 did not immunopreciptitate with anti-RANK in the absence of RANK expression.

EXAMPLE 7

This example describes isolation of a ligand for RANK, referred to as RANKL, by direct expression cloning. The ligand was cloned essentially as described in U.S. Ser. No. 08/249,189, filed May 24, 1994 (the relevant disclosure of which is incorporated by reference herein), for CD40L. Briefly, a library was prepared from a clone of a mouse thymoma cell line EL-4 (ATCC TIB 39), called EL-40.5, derived by sorting five times with biotinylated CD40/Fc fusion protein in a FACS (fluorescence activated cell sorter). The cDNA library was made using standard methodology; the plasmid DNA was isolated and transfected into sub-confluent CV1-EBNA cells using a DEAE-dextran method. Transfectants were screened by slide autoradiography for expression of RANKL using a two-step binding method with RANK/Fc fusion protein as prepared in Example 2 followed by radioiodinated goat anti-human IgG antibody.

A clone encoding a protein that specifically bound RANK was isolated and sequenced; the clone was referred to as 11H. An expression vector containing murine RANKL sequence, designated pDC406:muRANK-L (in *E. coli* DH10B), was deposited with the American Type Culture Collection, Rockville, Md. (ATCC) on Dec. 20, 1996, under terms of the Budapest Treaty, and given accession number 98284. The nucleotide sequence and predicted amino acid sequence of this clone are illustrated in SEQ ID NO:10. This clone did not contain an initiator methionine; additional, full-length clones were obtained from a 7B9 library (prepared substantially as described in U.S. patent 5,599,905, issued Feb. 4, 1997); the 5' region was found to be identical to that of human RANKL as shown in SEQ ID NO:12, amino acids 1 through 22, except for substitution of a Gly for a Thr at residue 9.

This ligand is useful for assessing the ability of RANK to bind RANKL by a number of different assays. For example, transfected cells expressing RANKL can be used in a FACS assay (or similar assay) to evaluate the ability of soluble RANK to bind RANKL. Moreover, soluble forms of RANKL can be prepared and used in assays that are known in the art (i.e., ELISA or BIAcore assays essentially as described in U.S. Ser. No. 08/249,189, filed May 24, 1994). RANKL is also useful in affinity purification of RANK, and as a reagent in methods to measure the levels of RANK in a sample. Soluble RANKL is also useful in inducing NF-κB activation and thus protecting cells that express RANK from apoptosis.

EXAMPLE 8

This example describes the isolation of a human RANK ligand (RANKL) using a PCR-based technique. Murine RANK ligand-specific oligonucleotide primers were used in PCR reactions using human cell line-derived first strand cDNAs as templates. Primers corresponded to nucleotides 478–497 and to the complement of nucleotides 858–878 of murine RANK ligand (SEQ ID NO:10). An amplified band approximately 400 bp in length from one reaction using the human epidermoid cell line KB (ATCC CCL-17) was gel purified, and its nucleotide sequence determined; the sequence was 85% identical to the corresponding region of murine RANK ligand, confirming that the fragment was from human RANKL.

To obtain full-length human RANKL cDNAs, two human RANKL-specific oligonucleotides derived from the KB PCR product nucleotide sequence were radiolabeled and used as hybridization probes to screen a human PBL cDNA library prepared in lambda gt10 (Stratagene, La Jolla, Calif.), substantially as described in U.S. Pat. No. 5,599,905, issued Feb. 4, 1997 . Several positive hybridizing plaques were identified and purified, their inserts subcloned into pBluescript SK⁻ (Stratagene, La Jolla, Calif.), and their nucleotide sequence determined. One isolate, PBL3, was found to encode most of the predicted human RANKL, but appeared to be missing approximately 200 bp of 5' coding region. A second isolate, PBL5 was found to encode much of the predicted human RANKL, including the entire 5' end and an additional 200 bp of 5' untranslated sequence.

The 5' end of PBL5 and the 3' end of PBL3 were ligated together to form a full length cDNA encoding human RANKL. The nucleotide and predicted amino acid sequence of the full-length human RANK ligand is shown in SEQ ID NO:12. Human RANK ligand shares 83% nucleotide and 84% amino acid identity with murine RANK ligand. A plasmid vector containing human RANKL sequence, designated pBluescript:huRANK-L (in *E. coli* DH10B), was deposited with the American Type Culture Collection, Rockville, Md. (ATCC) on Mar. 11, 1997 under terms of the Budapest Treaty, and given accession number 98354.

Murine and human RANKL are Type 2 transmembrane proteins. Murine RANKL contains a predicted 48 amino acid intracellular domain, 21 amino acid transmembrane domain and 247 amino acid extracellular domain. Human RANKL contains a predicted 47 amino acid intracellular domain, 21 amino acid transmembrane domain and 249 amino acid extracellular domain.

EXAMPLE 9

This example describes the chromosomal mapping of human RANK using PCR-based mapping strategies. Initial human chromosomal assignments were made using RANK and RANKL-specific PCR primers and a BIOS Somatic Cell Hybrid PCRable DNA kit from BIOS Laboratories (New Haven, Conn.), following the manufacturer's instructions. RANK mapped to human chromosome 18; RANK ligand mapped to human chromosome 13. More detailed mapping was performed using a radiation hybrid mapping panel Genebridge 4 Radiation Hybrid Panel (Research Genetics, Huntsville, Ala.; described in Walter, Mass. et al., *Nature Genetics* 7: 22–28, 1994). Data from this analysis was then submitted electronically to the MIT Radiation Hybrid Mapper (URL: http://www.genome.wi.mit.edu/cgi-bin/contig/rhmapper.pl) following the instructions contained therein. This analysis yielded specific genetic marker names which, when submitted electronically to the NCBI Entrez browser (URL: http://www3.ncbi.nlm.nih.gov/htbin-post/Entrez/query?db=c&form=0), yielded the specific map locations. RANK mapped to chromosome 18q22.1, and RANKL mapped to chromosome 13q14.

EXAMPLE 10

This example illustrates the preparation of monoclonal antibodies against RANKL. Preparations of purified recombinant RANKL, for example, or transfixed cells expressing high levels of RANKL, are employed to generate monoclonal antibodies against RANKL using conventional techniques, such as those disclosed in U.S. Pat. No. 4,411,993. DNA encoding RANKL can also be used as an immunogen, for example, as reviewed by Pardoll and Beckerleg in *Immunity* 3: 165, 1995. Such antibodies are likely to be useful in interfering with RANKL signaling (antagonistic or blocking antibodies), as components of diagnostic or research assays for RANKL or RANKL activity, or in affinity purification of RANKL.

To immunize rodents, RANKL immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 µg subcutaneously into a selected rodent, for example, BALB/c mice or Lewis rats. DNA may be given intradermally (Raz et al., *Proc. Natl. Acad. Sci. USA* 91: 9519, 1994) or intamuscularly (Wang et al., *Proc. Natl. Acad. Sci. USA* 90: 4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with RANKL, for example, by adaptations of the techniques disclosed by Engvall et al., *Immunochem.* 8: 871 (1971) and in U.S. Pat. No. 4,703,004. A preferred screening technique is the antibody capture technique described by Beckman et al., *J. Immunol.* 144: 4212 (1990). Positive clones are then injected into the peritoneal cavities of syngeneic rodents to produce ascites containing high concentrations (>1 mg/ml) of anti-RANK monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to RANKL protein. Using the methods described herein to monitor the activity of the mAbs, both blocking (i.e., antibodies that bind RANKL and inhibit binding to RANK) and non-blocking (i.e., antibodies that bind RANKL and do not inhibit binding) are isolated.

EXAMPLE 11

This example demonstrates that RANK expression can be up-regulated. Human peripheral blood T cells were purified by flow cytometry sorting or by negative selection using antibody coated beads, and activated with anti-CD3 (OKT3, Dako) coated plates or phytohemagglutinin in the presence or absence of various cytokines, including Interleukin-4 (IL-4),Transforming Growth Factor-β (TGF-β) and other commercially available cytokines ( IL1-α, IL-2, IL-3, IL-6, IL-7, IL-8, IL-10, IL-12, IL-15, IFN-γ, TNF-α). Expression of RANK was evaluated by FACS in a time course experiment for day 2 to day 8, using a mouse monoclonal antibody mAb144 (prepared as described in Example 3), as shown in the table below. Results are expressed as '+' to '++++' referring to the relative increase in intensity of staining with anti-RANK. Double labeling experiments using both anti-RANK and anti-CD8 or anti-CD4 antibodies were also performed.

TABLE 1

Upregulation of RANK by Cytokines

| Cytokine (concentration) | Results: |
|---|---|
| IL-4 (50 ng/ml) | + |
| TGF-β (5 ng/ml) | + to ++ |
| IL-4 (50 ng/ml) + TGF-β (5 ng/ml) | ++++ |
| IL1-α (10 ng/ml) | − |
| IL-2 (20 ng/ml) | − |
| IL-3 (25 ng/ml) | − |
| IL-7 (20 ng/ml) | − |
| IL-8 (10 ng/ml) | − |
| IL-10 (50 ng/ml) | − |
| IL-12 (10 ng/ml) | − |
| IL-15 (10 ng/ml) | − |
| IFN-γ (100 U/ml) | − |
| TNF-α (10 ng/ml) | − |

Of the cytokines tested, IL-4 and TGF-β increased the level of RANK expression on both CD8+ cytotoxic and CD4+ helper T cells from day 4 to day 8. The combination of IL-4 and TGF-β acted synergistically to upregulate expression of this receptor on activated T cells. This particular combination of cytokines is secreted by suppresser T cells, and is believed to be important in the generation of tolerance (reviewed in Mitchison and Sieper, *Z. Rheumatol.* 54: 141, 1995), implicating the interaction of RANK in regulation of an immune response towards either tolerance or induction of an active immune response.

EXAMPLE 12

This example illustrates the influence of RANK.Fc and hRANKL on activated T cell growth. The addition of TGFβ to anti-CD3 activated human peripheral blood T lymphocytes induces proliferation arrest and ultimately death of most lymphocytes within the first few days of culture. We tested the effect of RANK:RANKL interactions on TGFβ-treated T cells by adding RANK.Fc or soluble human RANKL to T cell cultures.

Human peripheral blood T cells ($7 \times 10^5$ PBT) were cultured for six days on anti-CD3 (OKT3, 5 µg/ml) and anti-Flag (M1, 5 µg/ml) coated 24 well plates in the presence of TGFβ (1 ng/ml) and IL-4 (10 ng/ml), with or without recombinant FLAG-tagged soluble hRANKL (1 µg/ml) or RANK.Fc (10 µg/ml). Viable T cell recovery was determined by triplicate trypan blue countings.

The addition of RANK.Fc significantly reduced the number of viable T cells recovered after six days, whereas soluble RANKL greatly increased the recovery of viable T cells (FIG. 1). Thus, endogenous or exogenous RANKL enhances the number of viable T cells generated in the presence of TGFβ. TGFβ, along with IL-4, has been implicated in immune response regulation when secreted by the $T_H3$/regulatory T cell subset. These T cells are believed to mediate bystander suppression of effector T cells. Accordingly, RANK and its ligand may act in an auto/paracrine fashion to influence T cell tolerance. Moreover, TGFβ is known to play a role in the evasion of the immune system effected by certain pathogenic or opportunistic organisms. In addition to playing a role in the development of tolerance, RANK may also play a role in immune system evasion by pathogens.

EXAMPLE 13

Figure 2:
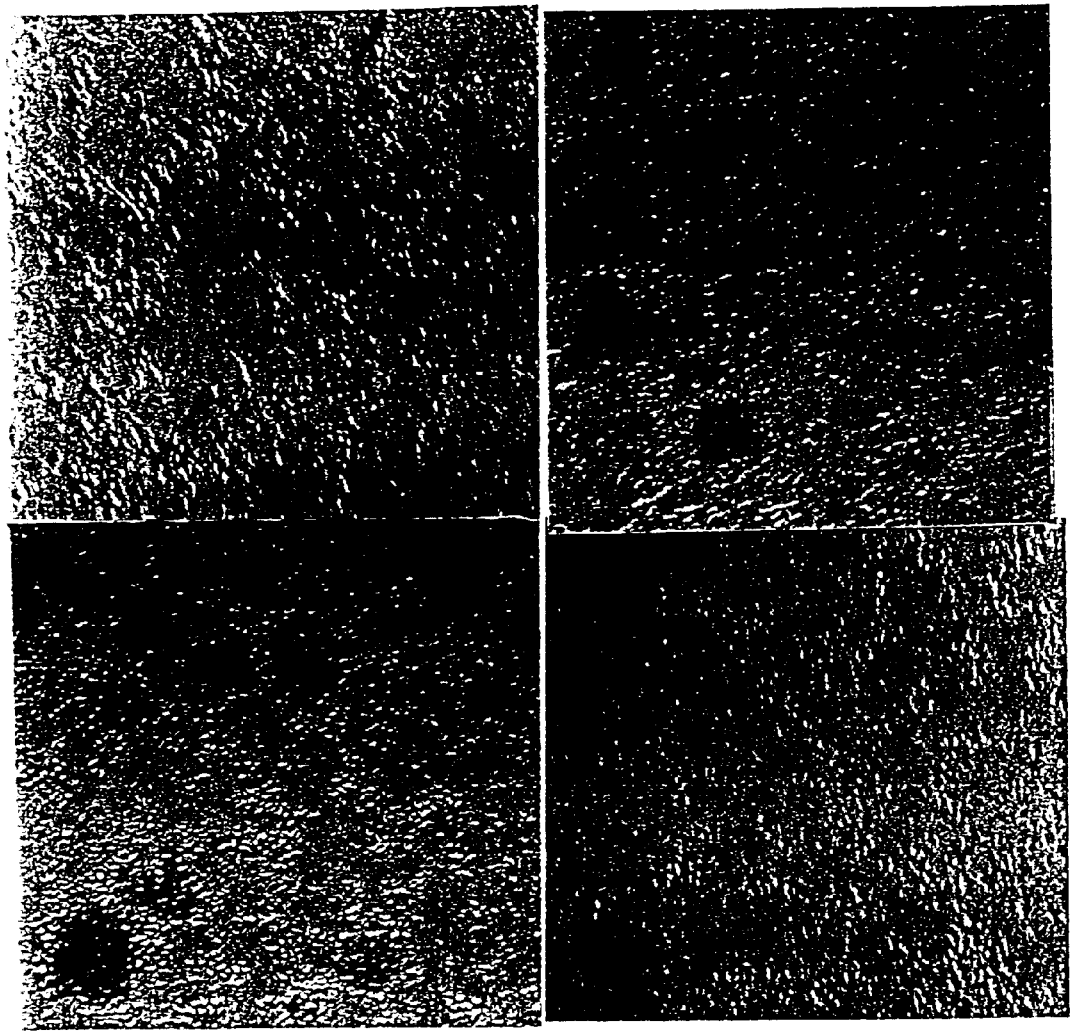
FIG. 2 illustrates the ability of RANKL to induce human DC cluster formation. Functionally mature dendritic cells (DC) were generated in vitro from CD34$^+$ bone marrow (BM) progenitors and cultured as described in Example 13. CD1a$^+$ DC were cultured in a cytokine cocktail alone (upper left panel), in cocktail plus CD40L (upper right), RANKL (lower left), or heat inactivated (ΔH) RANKL, and then photographed using an inversion microscope.

This example illustrates the influence of the interaction of RANK on $CD1a^+$ dendritic cells (DC). Functionally mature dendritic cells (DC) were generated in vitro from CD34+ bone marrow (BM) progenitors. Briefly, human BM cells from normal healthy volunteers were density fractionated using Ficoll medium and CD34+ cells immunoaffinity isolated using an anti-CD34 matrix column (Ceprate, CellPro). The CD34+ BM cells were then cultured in human GM-CSF (20 ng/ml), human IL-4 (20 ng/ml), human TNF-α (20 ng/ml), human CHO-derived Flt3L (FL; 100 ng/ml) in Super McCoy's medium supplemented with 10% fetal calf serum in a fully humidified 37° C. incubator (5% $CO_2$) for 14 days. CD1a+, HLA-DR+ DC were then sorted using a FACStar Plus™, and used for biological evaluation of RANK On human CD1a+ DC derived from CD34+ bone marrow cells, only a subset (20–30%) of CD1a+ DC expressed RANK at the cell surface as assessed by flow cytometric analysis. However, addition of CD40L to the DC cultures resulted in RANK surface expression on the majority of CD1a+ DC. CD40L has been shown to activate DC by enhancing in vitro cluster formation, inducing DC morphological changes and upregulating HLA-DR, CD54, CD58, CD80 and CD86 expression Addition of RANKL to DC cultures significantly increased the degree of DC aggregation and cluster formation above control cultures, similar to the effects seen with CD40L (FIG. 2). Sorted human CD1a+ DC were cultured in a cytokine cocktail (GM-CSF, IL-4, TNF-α and FL) (upper left panel), in cocktail plus CD40L (1 µg/ml) (upper right), in cocktail plus RANKL (1 µg/ml) (lower left), or in cocktail plus heat inactivated (ΔH) RANKL (1 µg/ml) (lower right) in 24-well flat bottomed culture plates in 1 ml culture media for 48–72 hours and then photographed using an inversion microscope. An increase in DC aggregation and cluster formation above control cultures was not evident when heat inactivated RANKL was used, indicating that this effect was dependent on biologically active protein. However, initial phenotypic analysis of adhesion molecule expression indicated that RANKL-induced clustering was not due to increased levels of CD2, CD11 a, CD54 or CD58.

Figure 3:
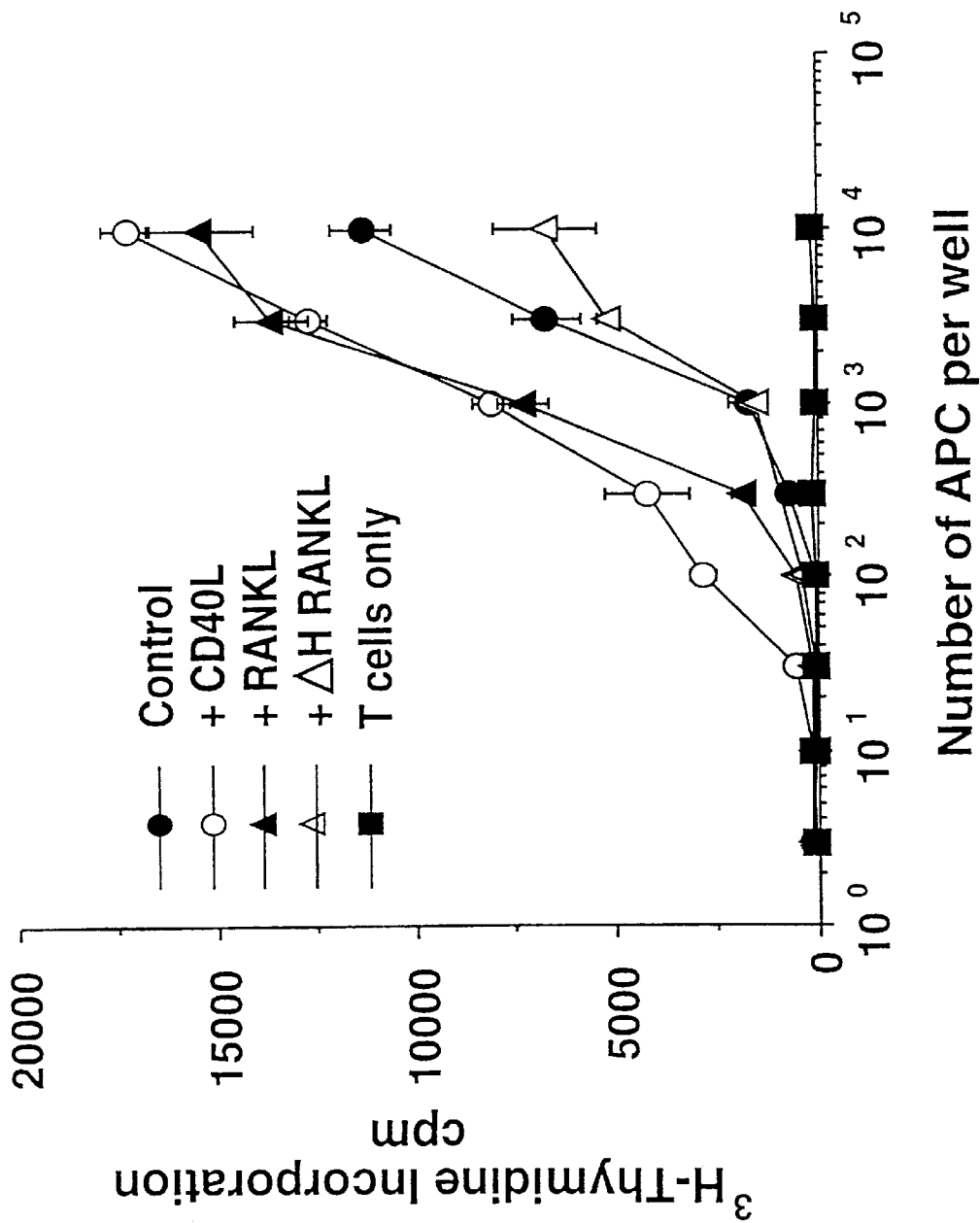
FIG. 3 demonstrates that RANKL enhances DC allostimulatory capacity. Allogeneic T cells were incubated with varying numbers of irradiated DC cultured as described in Example 13. The cultures were pulsed with [$^3$H]-thymidine and the cells harvested onto glass fiber sheets for counting. Values represent the mean ± standard deviation (SD) of triplicate cultures.

The addition of RANKL to CD1a+ DC enhanced their allo-stimulatory capacity in a mixed lymphocyte reaction (MLR) by at least 3- to 10-fold, comparable to CD40L-cultured DC (FIG. 3). Allogeneic T cells (1×10$^5$) were incubated with varying numbers of irradiated (2000 rad) DC cultured as indicated above for FIG. 2 in 96-well round bottomed culture plates in 0.2 ml culture medium for four days. The cultures were pulsed with 0.5 mCi [$^3$H]-thymidine for eight hours and the cells harvested onto glass fiber sheets for counting on a gas phase β counter. The background counts for either T cells or DC cultured alone were <100 cpm. Values represent the mean ± SD of triplicate cultures. Heat inactivated RANKL had no effect. DC allo-stimulatory activity was not further enhanced when RANKL and CD40L were used in combination, possibly due to DC functional capacity having reached a maximal level with either cytokine alone. Neither RANKL nor CD40L enhanced the in vitro growth of DC over the three day culture period. Unlike CD40L, RANKL did not significantly increase the levels of HLA-DR expression nor the expression of CD80 or CD86.

RANKL can enhance DC cluster formation and functional capacity without modulating known molecules involved in cell adhesion (CD18, CD54), antigen presentation (HLA-DR) or costimulation (CD86), all of which are regulated by CD40/CD40L signaling. The lack of an effect on the expression of these molecules suggests that RANKL may regulate DC function via an alternate pathway(s) distinct from CD40/CD40L. Given that CD40L regulates RANK surface expression on in vitro-generated DC and that CD40L is upregulated on activated T cells during DC-T cell interactions, RANK and its ligand may form an important part of the activation cascade that is induced during DC-mediated T cell expansion. Furthermore, culture of DC in RANKL results in decreased levels of CD1b/c expression, and increased levels of CD83. Both of these molecules are similarly modulated during DC maturation by CD40L (Caux et al. *J. Exp. Med.* 180: 1263; 1994), indicating that RANKL induces DC maturation.

Dendritic cells are referred to as "professional" antigen presenting cells, and have a high capacity for sensitizing MHC-restricted T cells. There is growing interest in using dendritic cells ex vivo as tumor or infectious disease vaccine adjuvants (see, for example, Romani, et al., *J. Exp. Med.*, 180: 83, 1994). Therefore, an agent such as RANKL that induces DC maturation and enhances the ability of dendritic cells to stimulate an immune response is likely to be useful in immunotherapy of various diseases.

EXAMPLE 14

This example describes the isolation of the murine homolog of RANK, referred to as muRANK. MuRANK was isolated by a combination of cross-species PCR and colony hybridization. The conservation of Cys residues in the Cys-rich pseudorepeats of the extracellular domains of TNFR superfamily member proteins was exploited to design human RANK-based PCR primers to be used on murine first strand cDNAs from various sources. Both the sense upstream primer and the antisense downstream primer were designed to have their 3' ends terminate within Cys residues.

The upstream sense primer encoded nucleotides 272–295 of SEQ ID NO:5 (region encoding amino acids 79–86); the downstream antisense primer encoded the complement of nucleotides 409–427 (region encoding amino acids 124–130). Standard PCR reactions were set up and run, using these primers and first strand cDNAs from various murine cell line or tissue sources. Thirty reaction cycles of 94° C. for 30 seconds, 50° C. for 30 seconds, and 72° C. for 20 seconds were run. PCR products were anlyzed by electrophoresis, and specific bands were seen in several samples. The band from one sample was gel purified and DNA sequencing revealed that the sequence between the primers was approximately 85% identical to the corresponding human RANK nucleotide sequence.

A plasmid based cDNA library prepared from the murine fetal liver epithelium line FLE18 (one of the cell lines identified as positive in the PCR screen) was screened for full-length RANK cDNAs using murine RANK-specific oligonucleotide probes derived from the murine RANK sequence determined from sequencing the PCR product. Two cDNAs, one encoding the 5' end and one encoding the 3' end of full-length murine RANK (based on sequence comparison with the full-length human RANK) were recombined to generate a full-length murine RANK cDNA. The nucleotide and amino acid seqeunce of muRANK are shown in SEQ ID Nos: 14 and 15.

The cDNA encodes a predicted Type 1 transmembrane protein having 625 amino acid residues, with a predicted 30 amino acid signal sequence, a 184 amino acid extracellular domain, a 21 amino acid transmembrane domain, and a 390 amino acid cytoplasmic tail. The extracellular region of muRANK displayed significant amino acid homology (69.7% identity, 80.8% similarity) to huRANK. Those of skill in the art will recognize that the actual cleavage site can be different from that predicted by computer; accordingly, the N-terminal of RANK may be from amino acid 25 to amino acid 35.

Other members of the TNF receptor superfamily have a region of amino acids between the transmembrane domain and the ligand binding domain that is referred to as a 'spacer' region, which is not necessary for ligand binding. In muRANK, the amino acids between 197 and 214 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 214, and 197 of SEQ ID NO:14, although other amino acids in the spacer region may be utilized as a C-terminus.

EXAMPLE 15

This example illustrates the preparation of several different soluble forms of RANK and RANKL. Standard techniques of restriction enzyme cutting and ligation, in combination with PCR-based isolation of fragments for which no convenient restriction sites existed, were used. When PCR was utilized, PCR products were sequenced to ascertain whether any mutations had been introduced; no such mutations were found.

In addition to the huRANK/Fc described in Example 2, another RANK/Fc fusion protein was prepared by ligating DNA encoding amino acids 1–213 of SEQ ID NO:6, to DNA encoding amino acids 3–232 of the Fc mutein described previously (SEQ ID NO:8). A similar construct was prepared for murine RANK, ligating DNA encoding amino acids 1–213 of full-length murine RANK (SEQ ID NO:15) to DNA encoding amino acids 3–232 of the Fc mutein (SEQ ID NO:8).

A soluble, tagged, poly-His version of huRANKL was prepared by ligating DNA encoding the leader peptide from the immunoglobulin kappa chain (SEQ ID NO:16) to DNA encoding a short version of the FLAG™ tag (SEQ ID NO:17), followed by codons encoding Gly Ser, then a poly-His tag (SEQ ID NO:18), followed by codons encoding Gly Thr Ser, and DNA encoding amino acids 138–317 of SEQ ID NO:13. A soluble, poly-His tagged version of murine RANKL was prepared by ligating DNA encoding the CMV leader (SEQ ID NO:9) to codons encoding Arg Thr Ser, followed by DNA encoding poly-His (SEQ ID NO:18) followed by DNA encoding amino acids 119–294 of SEQ ID NO:11.

A soluble, oligomeric form of huRANKL was prepared by ligating DNA encoding the CMV leader (SEQ ID NO:9) to a codon encoding Asp followed by DNA ending a trimerformer "leucine" zipper (SEQ ID NO:19), then by codons encoding Thr Arg Ser followed by amino acids 138–317 of SEQ ID NO:13.

These and other constructs are prepared by routine experimentation. The various DNAs are then inserted into a suitable expression vector, and expressed. Particularly preferred expression vectors are those which can be used in mammalian cells. For example, pDC409 and pDC304, described herein, are useful for transient expression. For stable transfection, the use of CHO cells is preferred; several useful vectors are described in U.S. Ser. No. 08/785,150, now allowed, for example, one of the 2A5-3 λ-derived expression vectors discussed therein.

EXAMPLE 16

This example demonstrates that RANKL expression can be up-regulated on murine T cells. Cells were obtained from mesenteric lymph nodes of C57BL/6 mice, and activated with anti-CD3 coated plates, Concanavalin A (ConA) or phorbol myristate acetate in combination with ionomycin (anti-CD3: 500A2; Immunex Corporation, Seattle Wash.; ConA, PMA, ionomycin, Sigma, St. Louis, Mo.) substantially as described herein, and cultured from about 2 to 5 days. Expression of RANKL was evaluated in a three color analysis by FACS, using antibodies to the T cell markers CD4, CD8 and CD45RB, and RANK/Fc, prepared as described herein.

RANKL was not expressed on unstimulated murine T cells. T cells stimulated with either anti-CD3, ConA, or PMA/ionomycin, showed differential expression of RANKL: $CD4^+/CD45RB^{Lo}$ and $CD4^+/CD45RB^{Hi}$ cells were positive for RANKL, but CD8+ cells were not. RANKL was not observed on B cells, similar to results observed with human cells.

EXAMPLE 17

This example illustrates the effects of murine RANKL on cell proliferation and activation. Various cells or cell lines representative of cells that play a role in an immune response (murine spleen, thymus and lymphnode) were evaluated by culturing them under conditions promoting their viability, in the presence or absence of RANKL. RANKL did not stimulate any of the tested cells to proliferate. One cell line, a macrophage cell line referred to as RAW 264.7 (ATCC accession number TIB 71) exhibited some signs of activation.

RAW cells constitutively produce small amounts of TNF-α. Incubation with either human or murine RANKL enhanced production of TNF-α by these cells in a dose dependent manner. The results were not due to contamination of RANKL preparations with endotoxin, since boiling RANKL for 10 minutes abrogated TNF-α production, whereas a similar treatment of purified endotoxin (LPS) did not affect the ability of the LPS to stimulate TNF-α production. Despite the fact that RANKL activated the macrophage cell line RAW T64.7 for TNF-α production, neither human RANKL nor murine RANKL stimulated nitric oxide production by these cells.

EXAMPLE 18

This example illustrates the effects of murine RANKL on growth and development of the thymus in fetal mice. Pregnant mice were injected with 1 mg of RANK/Fc or vehicle control protein (murine serum albumin; MSA) on days 13, 16 and 19 of gestation. After birth, the neonates continued to be injected with RANK/Fc intraperitoneally (IP) on a daily basis, beginning at a dose of 1 μg, and doubling the dose about every four days, for a final dosage of 4 μg. Neonates were taken at days 1, 8 and 15 post birth, their thymuses and spleens harvested and examined for size, cellularity and phenotypic composition.

A slight reduction in thymic size at day 1 was observed in the neonates born to the female injected with RANK/Fc; a similar decrease in size was not observed in the control neonates. At day 8, thymic size and cellularity were reduced by about 50% in the RANK/Fc-treated animals as compared to MSA treated mice. Phenotypic analysis demonstrated that the relative proportions of different T cell populations in the thymus were the same in the RANK/Fc mice as the control mice, indicating that the decreased cellularity was due to a global depression in the number of thymic T cells as opposed to a decrease in a specific population(s). The RANK/Fc-treated neonates were not significantly different from the control neonates at day 15 with respect to either size, cellularity or phenotype of thymic cells. No significant differences were observed in spleen size, cellularity or composition at any of the time points evaluated. The difference in cellularity on day 8 and not on day 15 may suggest that RANK/Fc may assert its effect early in thymic development.

EXAMPLE 19

This example demonstrates that the C-terminal region of the cytoplasmic domain of RANK is important for binding of several different TRAF proteins. RANK contains at least two recognizable PXQX(X)T motifs that are likely TRAF docking sites. Accordingly, the importance of various regions of the cytoplasmic domain of RANK for TRAF binding was evaluated. A RANK/GST fusion protein was prepared substantially as described in Smith and Johnson, *Gene* 67: 31 (1988), and used in the preparation of various truncations as described below.

Comparison of the nucleotide sequence of murine and human RANK indicated that there were several conserved regions that could be important for TRAF binding. Accordingly, a PCR-based technique was developed to facilitate preparation of various C-terminal truncations that would retain the conserved regions. PCR primers were designed to introduce a stop codon and restriction enzyme site at selected points, yielding the truncations described in Table 1 below. Sequencing confirmed that no undesired mutations had been introduced in the constructs.

Radio-labeled ($^{35}$S-Met, Cys) TRAF proteins were prepared by in vitro translation using a commercially available reticulocyte lysate kit according to manufacturer's instructions (Promega). Truncated GST fusion proteins were purified substantially as described in Smith and Johnson (supra).

Briefly, *E. coli* were transfected with an expression vector encoding a fusion protein, and induced to express the protein. The bacteria were lysed, insoluble material removed, and the fusion protein isolated by precipitation with glutathione-coated beads (Sepahrose 4B, Pharmacia, Uppsala Sweden)

The beads were washed, and incubated with various radiolabeled TRAF proteins. After incubation and wash steps, the fusion protein/TRAF complexes were removed from the beads by boiling in 0.1% SDS+β-mercaptoethanol, and loaded onto 12% SDS gels (Novex). The gels were subjected to autoradiography, and the presence or absence of radiolabeled material recorded. The results are shown in Table 2 below.

TABLE 2

Binding of Various TRAF Proteins to the Cytoplasmic Domain of RANK

| C terminal Truncations: | E206-S339 | E206-Y421 | E206-M476 | E206-G544 | Full length |
|---|---|---|---|---|---|
| TRAF1 | − | − | − | − | ++ |
| TRAF2 | − | − | − | − | ++ |
| TRAF3 | − | − | − | − | ++ |
| TRAF4 | − | − | − | − | − |
| TRAF5 | − | − | − | − | + |
| TRAF6 | − | + | + | + | ++ |

These results indicate that TRAF1, TRAF2, TRAF3, TRAF 5 and TRAF6 bind to the most distal portion of the RANK cytoplasmic domain (between amino-acid G544 and A616). TRAF6 also has a binding site between S339 and Y421. In this experiment, TRAF5 also bound the cytoplasmic domain of RANK.

We claim:

1. An isolated DNA selected from the group consisting of:
   (a) a DNA encoding a protein comprising amino acids x through 616 of SEQ ID NO:6, wherein x is selected from the group consisting of amino acid 1 and any one of amino acids 24 through 33 of SEQ ID NO:6;
   (b) a DNA encoding a protein comprising amino acids x through 625 of SEQ ID NO:15, wherein x is selected from the group consisting of amino acid 1 and any one of amino acids 25 through 35 of SEQ ID NO:15;
   (c) DNA encoding a polypeptide comprising amino acids x through y of SEQ ID NO:6, wherein x is selected from the group consisting of amino acid 1 and any one of amino acids 24 through 33 of SEQ ID NO:6, and y is selected from the group consisting of any one of amino acids 196 through 213;
   (d) DNA encoding a polypeptide comprising amino acids x through y of SEQ ID NO:15, wherein x is selected from the group consisting of amino acid 1 and any one of amino acids 25 through 35 of SEQ ID NO:15, and y is selected from the group consisting of any one of amino acids 197 through 214; and
   (e) DNA molecules encoding fragments of proteins encoded by the DNA of (a)–(d), wherein the fragment is capable of binding RANKL or binding a TRAF.

2. An isolated DNA which encodes a polypeptide comprising amino acids x through y of SEQ ID NO:6, wherein x is selected from the group consisting of amino acid 1 and any one of amino acids 24 through 33 of SEQ ID NO:6, and y is selected from the group consisting of any one of amino acids 196 through 213.

3. The isolated DNA of claim 2, which further comprises a DNA encoding a polypeptide selected from the group consisting of an immunoglobulin Fc domain, an immunoglobulin Fc mutein, a FLAG™ tag, a peptide comprising at least about 6 His residues, a leucine zipper, and combinations thereof.

4. A recombinant expression vector comprising a DNA sequence according to claim 1.

5. A recombinant expression vector comprising a DNA sequence according to claim 2.

6. A recombinant expression vector comprising a DNA sequence according to claim 3.

7. A host cell transformed or transfected with an expression vector according to claim 4.

8. A host cell transformed or transfected with an expression vector according to claim 5.

9. A host cell transformed or transfected with an expression vector according to claim 6.

10. A process for preparing a protein, comprising culturing a host cell according to claim 7 under conditions promoting expression of the protein.

11. A process for preparing a protein, comprising culturing a host cell according to claim 8 under conditions promoting expression of the protein.

12. A process for preparing a protein, comprising culturing a host cell according to claim 9 under conditions promoting expression of the protein.

13. An isolated DNA that is at least 9 nucleotides in length, and which is a fragment of the DNA of the coding region of SEQ ID NO:5.

14. An isolated DNA encoding a protein comprising the amino acid sequence x through 616 of SEQ ID NO:6, wherein x is selected from the group consisting of amino acid 1 and any one of amino acids 24 through 33 of SEQ ID NO:6.

* * * * *

UNITED STATES PATENT AND TRADEMARK OFFICE
CERTIFICATE OF CORRECTION

| | | |
|---|---|---|
| PATENT NO. | : 6,017,729 | Page 1 of 1 |
| APPLICATION NO. | : 08/996139 | |
| DATED | : January 25, 2000 | |
| INVENTOR(S) | : Dirk M. Anderson | |

It is certified that error appears in the above-identified patent and that said Letters Patent is hereby corrected as shown below:

Title page, Item [75] Inventors:   "Dirk M. Anderson; Laurent Galibert, both of Seattle, Wash.; Eugene Maraskovsky, Caulfield Nth. Australia" should read -- Dirk M. Anderson, Seattle, Wash. --

Signed and Sealed this

Twenty-seventh Day of November, 2012

David J. Kappos
*Director of the United States Patent and Trademark Office*